United States Patent [19]

Bodary et al.

[11] Patent Number: 5,726,037

[45] Date of Patent: Mar. 10, 1998

[54] HOST CELLS AND METHOD OF PRODUCING SOLUBLE ANALOGUES OF INTEGRINS

[75] Inventors: Sarah C. Bodary; Cornelia M. Gorman; John W. McLean, all of San Francisco; Mary A. Napier, Hillsborough, all of Calif.

[73] Assignee: Genentech, Inc., San Francisco, Calif.

[21] Appl. No.: 444,792

[22] Filed: May 19, 1995

Related U.S. Application Data

[62] Division of Ser. No. 380,227, Jan. 30, 1995, abandoned, which is a continuation of Ser. No. 218,878, Mar. 28, 1994, abandoned, which is a continuation of Ser. No. 821,337, Jan. 13, 1992, abandoned, which is a continuation of Ser. No. 444,490, Dec. 1, 1989, abandoned, which is a continuation-in-part of Ser. No. 290,224, Dec. 22, 1988, abandoned.

[51] Int. Cl.$^6$ .............................. C12N 5/10; C12N 15/12
[52] U.S. Cl. ..................... 435/69.1; 435/697; 435/325; 435/326; 435/252.3
[58] Field of Search ................... 435/69.7, 69.1, 435/252.3, 240.2, 325, 326

[56] References Cited

U.S. PATENT DOCUMENTS

4,761,371   8/1988   Bell et al. .............................. 435/69.1

FOREIGN PATENT DOCUMENTS

| 139416 | 5/1985 | European Pat. Off. . |
|---|---|---|
| 244221 | 11/1987 | European Pat. Off. . |
| 244267 | 11/1987 | European Pat. Off. . |
| 278776 | 8/1988 | European Pat. Off. . |
| WO 89/00200 | 1/1989 | WIPO . |
| WO 91/19511 | 12/1991 | WIPO . |

OTHER PUBLICATIONS

Argraves et al., "Amino Acid Sequence of the Human Fibronectin Receptor" *Journal of Cell Biology* 105:1183–1190 (Sep. 1987).

Argraves et al., "cDNA Sequences from the α subunit of the fibronectin receptor predict a transmembrane domain and a short cytoplasmic peptide" *Journal of Biological Chemistry* 261(28):12922–12924 (Oct. 5, 1986).

Arnaout et al., "Expression of a soluble and functional form of the human B2 integrin CD11b/CD18" *Journal of Cell Biology* 111(5):768 (1990).

Arnaout, A. M., et al., "Amino acid sequence of the alpha subunit of human leukocyte adhesion receptor mo1 complement receptor type 3" *Journal of Cell Biology* 106:2153–2158 (1988).

Bennett et al., "Expression of Human Platelet Glycoprotein IIb in Cult. Mamm. Cells." *61st Scientific Sessions 1234* (1988).

Berman et al., "Biosynthesis and Function of Membrane Bound and Secreted Forms of Recombinant CD11b/CD18 (Mac-1)" *J. Cell. Biochem.* 52:183–195 (1993).

Bodary et al., "Expression of recombinant platelet glycoprotein IIbIIIa results in a functional fibrinogen–binding complex" *Journal of Biological Chemistry* 264(32):18859–18862 (1989).

Boulianne, G. L. et al., "Production of functional chimaeric mouse/human antibody" *Nature* 312 (5995):643–646 (Dec. 1984).

Bray et al., "Physical linkage of the genes for platelet membrane glycoproteins IIb and IIIa" *Proc. Natl. Acad. Sci. USA* 85:8663–8687 (Nov. 1988).

Bray et al., "Platelet Glycoprotein IIb" *J. Clin. Invest.* 80:1812–1817 (Dec. 1987).

Buck and Horwitz, "Cell Surface Receptors for extracellular matrix molecules" *Ann. Rev. Cell Biol.* 3:179–205 (1987).

Chothia, "Principles that Determine the Structre of Proteins" *Annual Review of Biochem.* 53:537–572 (1984).

Cierniewski et al., "Palmitylation of the glycoprotein IIb–IIIa complex in human blood platelets" *Journal of Biological Chemistry* 264(21):12158–12164 (1989).

Corbi et al., "cDNA cloning and complete primary structure of the α subunit of a leukocyte adhesion glycoprotein" *EMBO Journal* 6(13):4023–4028 (1987).

Corbi et al., "The human leukocyte adhesion glycoprotein mac–1 (complement receptor type 3, CD11b) α subunit" *Journal of Biological Chemistry* 263(25):12403–12411 (1988).

Cosgrove et al., "A genomic clone encoding the α chain of the OKM1, LFA–1, and platelet glycoprotein IIb–IIIa molecules" *Proc. Natl. Acad. Sci. USA* 83:752–756 (1986).

Devlin et al., "Alteration of amino–terminal codons of human granulocyte–colony–stimulating factor increases expression levels and allows efficient processing by methionine aminopeptidase in *Escherichia coli*" *Gene* 65:13–22 (1988).

Doyle et al., "Analysis of progressive deletions of the transmembrane and cytoplasmic domains of influenza hemagglutinin" *Journal of Cell Biology* 103:1193–1204 (1986).

Doyle et al., "Mutations in the cytoplasmic domain of the influenza virus hemagglutinin affect different stages of intracellular transport" *Journal of Cell Biology* 100:704–714 (1985).

Early et al., "Two mRNAs can be produced from a single immunoglobulin μ Gene by alternative RNA processing pathways" *Cell* 20:313–319 (1980).

(List continued on next page.)

*Primary Examiner*—John Ulm
*Assistant Examiner*—Karen E. Brown
*Attorney, Agent, or Firm*—Wendy M. Lee; Deirdre L. Conley

[57] ABSTRACT

Methods are provided for the preparation in recombinant host cells of biologically active soluble variants of discretely encoded, heteromultimer polypeptide receptors. Such variants are synthesized by the secretion from recombinant transformants of transmembrane-modified heteromultimer receptors. Preferred receptors are extracellular matrix, cell surface, or plasma protein-binding receptors such as GPIIb-IIIa.

11 Claims, 14 Drawing Sheets

OTHER PUBLICATIONS

Falkner and Zachau, "Expression of mouse immunoglobulin genes in monkey cells" *Nature* 298:286–288 (1982).

Fisher et al., "HIV infection is blocked in vitro by recombinant soluble CD4" *Nature* 331:76–86 (1988).

Fitzgerald et al., "Comparison of cDNA–derived protein sequences of the human fibronectin and vitronectin receptor α–subunits and platelet glycoprotein IIb" *Biochemistry* 26:8158–8165 (1987).

Fitzgerald et al., "Protein Sequence of Endothelial Glycoprotein IIIa Derived from a cDNA Clone" *Journal of Biological Chemistry* 262:3936–3939 (1987).

Garoff, Henry, "Using recombinant DNA techniques to study protein targeting in the eucaryotic cell" *Ann. Rev. Cell Biol.* 1:403–445 (1985).

Gascoigne et al., "Secretion of a chimeric T–cell receptor–immunoglobulin protein" *Proc. Natl. Acad. Sci. USA* 84:2936–2940 (1987).

Gething & Sambrook, "Cell–surface expression of influenza haemagglutinin from a cloned DNA copy of the RNA gene" *Nature* 293:620–625 (1981).

Gething and Sambrook, "Construction of influenza haemagglutinin genes that code for intracellular and secreted forms of the protein" *Nature* 300:598–603 (1982).

Gething et al., "Expression of wild–type and mutant forms of influenza hemagglutinin: the role of folding in intracellular transport" *Cell* 46:939–950 (1986).

Gething et al., "Mutational analysis of the structure and function of the influenza virus hemagglutinin" *Current Topics in Membranes and Transport*, Academic Press, Chapter 2, vol. 23:17–41 (1985).

Ginsberg et al., "Cytoadhesins, integrins, and platelets" *Thromb. Haemost.* 59(1):1–6 (1988).

Groux et al., "Suppressor effects and cyclic AMP accumulation by the CD29 molecule of CD4+ lymphocytes" *Nature* 339:152–154 (1989).

Heidenreich et al., "Organization of the gene for platelet glycoprotein IIb" *Biochemistry* 29:1232–1244 (1990).

Hibbs et al., "The Cytoplasmic Domain of LFA–1 B subunit: sites required for binding . . . " *Journal of Experimental Medicine* 174:1227–1238 (Nov. 1991).

Holzmann et al., "Identification of a Murine Peyer's Patch–specific lymphocyte homing receptor as an integrin molecule with an α chain homologous to human VLA–4α" *Cell* 56:37–46 (1989).

Hurtley and Helenius, "Protein oligomerization in the endoplasmic reticulum" *Ann. Rev. Cell Biol.* 5:277–307 (1989).

Hynes, RO, "Integrins: A Family of Cell Surface Receptors" *Cell* 48:549–554 (1987).

Johnson et al., "Properties of the Insulin Receptor Ectodomain" *Proc. Natl. Acad. Sci. USA* 85:7516–7520 (1988).

Karnik et al., "Structure–function studies on bacteriorhodopsin" *Journal of Biological Chemistry* 262(19):9255–9263 (1987).

Kishimoto et al., "Cloning of the β Subunit of the Leukocyte Adhesion Proteins: Homology to an Extracellular Matrix Receptor Defines a Novel Supergene Family" *Cell* 48:681–690 (1987).

Kishimoto et al., "Leukocyte Adhesion Molecules" *Springer–Verlag* (Springer et al., ed.) p. 15.

Kohler, G., "Immunoglobulin chain loss in hybridoma lines" *Proc. Natl. Acad. Sci. USA* 77(4):2197–2199 (1980).

Kozak, M., "At least six nucleotides preceding the AUG initiator codon enhance translation in mammalian cells" *J. Mol. Biol.* 196:947–950 (1987).

Krangel et al., "Characterization of B Lymphoblastoid Cell Line Mutant that Secretes HLA–A2" *J. Immunol.* 132(6):2984–2991 (1984).

Larson et al., "Cloning of the alpha subunit of human LFA–1" *J. Cell. Biochem.* S11D:272 (1987).

Larson et al., "Primary structure of the leukocyte function–associated molecule–1 α subunit: an integrin with an embedded domain defining a protein superfamily" *Journal of Cell Biology* 108:703–712 (1989).

Loeb and Drickamer, "The chicken receptor for endocytosis of glycoproteins contains a cluster of N–acetylglucosamine–binding sites" *Journal of Biological Chemistry* 262(7):3022–3029 (1987).

Loftus et al., "Molecular cloning and chemical synthesis of a region of platelet glycoprotein IIb involved in adhesive function" *Proc. Natl. Acad. Sci. USA* 84:7114–7118 (1987).

MacKrell et al., "The lethal myospheroid gene of Drosophila encodes a membrane protein homologous to vertebrate integrin B subunits" *Proc. Natl. Acad. Sci. USA* 85:2633–2637 (Apr. 1988).

Mariuzza and Winter, "Secretion of a homodimeric VαCk T–cell receptor–immunoglobulin chimeric protein" *Journal of Biological Chemistry* 264(13):7310–7316 (1989).

Munro, "Uses of chimaeric antibodies" *Nature* 312:597 (1984).

Neuberger et al., "Recombinant antibodies possessing novel effector functions" *Nature* 312(5995):604–608 (Dec. 1984).

O'Toole et al, "Efficient surface expression of platelet GPI–Ib–IIIa Requires both subunits" *Blood* 74(1):14–18 (1989).

Owen and Lamb, "The T cell antigen receptor" *Immune Recognition* (IRL Press) pp. 37–42 (1988).

Phillips et al., "the Platelet Membrane Glycoprotein IIb–IIIa Complex" *Blood* 71(4):831–843 (1988).

Phillips et al., "The Platelet Membrane Glycoprotein IIb/IIIa Complex" *Annals N.Y. Acad. Sci.* 509:177–187 (1987).

Poncz et al., "Structure of the Platelet Membrane Glycoprotein IIb" *Journal of Biological Chemistry* 262(18):8476–8482 (Jun. 25, 1987).

Rogers et al., "Gene segments encoding transmembrane carboxyl termini of immunoglobulin gamma chains" *Cell* 26:19–27 (1981).

Rogers et al., "Two mRNAs can be produced from a single immunoglobulin μ gene by alternative RNA processing pathways" *Cell* 20:303–312 (1980).

Rosa et al., "Cloning of Glycoprotein IIIa cDNA from human erythroleukemia cells and localization of the gene to chromosome 17" *Blood* 72(2):593–600 (Aug. 1988).

Rose and Bergmann, "Expression from Cloned cDNA of Cell–surface Secreted Forms of the Glycoprotein of Vesicular Stomatitis Virus in Eucaryotic Cells" *Cell* 30:753–762 (1982).

Rose and Doms, "Regulation of protein export from the endoplasmic reticulum" *Ann. Rev. Cell Biol.* 4:257–288 (1988).

Rouslahti et al., "New perspectives in cell adhesion: RGD and Integrins" *Science* 238:491–497 (1987).

Rupp et al., "Identical VB T–cell receptor genes used in alloreactive cytotoxic and antigen plus I–A specific helper T cells" *Nature* 315:425–427 (1985).

Sharon et al., "Expression of a $V_hC_k$ Chimaeric Protein in Mouse Myeloma Cells" *Nature* 309:364–367 (1984).

Smith et al., "Blocking of HIV-1 Infectivity by a Soluble, Secreted Form of the CD4 Antigen" *Science* 238:1704–1707 (1987).

Suzuki and Naitoh, "Amino acid sequence of a novel integrin B4 subunit and primary expression of the mRNA in epithelial cells" *EMBO Journal* 9(3):757–763 (1990).

Suzuki et al., "Amino acid sequence of the vitronectin receptor α subunit and comparative expression of adhesion receptor mRNAs*" *Journal of Biological Chemistry* 262(29):14080–14085 (Oct. 15, 1987).

Sveda et al., "Influenza virus hemagglutinin containing an altered hydrophobic carboxy terminus accumulates intracellularly" *Journal of Virology* 49(1):223–228 (1984).

Tamkun et al., "Structure of Integrin, a Glycoprotein Involved in the Transmembrane Linkage between Fibronectin and Actin" *Cell* 46:271–282 (1986).

Thiagarajan et al., "A human erythroleukemia cell line synthesizes a functionally active glycoprotein IIb–IIIa complex capable of binding fibrinogen" *Biochimica et Biophysica Acta* 924:127–134 (1987).

Traunecker et al., "Soluble CD4 molecules neutralize human immunodeficiency virus" *Nature* 331:84–86 (1988).

Van Driel et al., "Self–association of the low density lipoprotein receptor mediated by the cytoplasmic domain" *Journal of Biological Chemistry* 262(33):16127–16134 (1987).

Wills et al., "Mutations of the Rous Sarcoma Virus env Gene that affect the transport and subcellular location of the glycoprotein products" *Journal of Cell Biology* 99:2011–2023 (1984).

Yuan et al., "Cloning and sequence analysis of a novel β 2–related integrin transcript from T lymphocytes: homology of integrin cysteine–rich repeats to domain III of laminin B chains" *Int–Immunol* (published erratum appears in Int Immunol 1991 Dec;3(12):1373–4) 2(11):1097–1108 (1990).

Zimrin et al., "Structure of Platelet of Glycoprotein IIIa" *J. Clin. Invest.* 81:1470–1475 (May 1988).

Fig. 1(a)

```
                                                                                                         sau96I
                                                                                                         avaII
                                                                                           PpuMI         fnu4HI
                                                                                           nlaIV         bbvI
                                                                                           ecoO109I
                                                                                fnu4HI
                                                                                bbvI
                                                                       fnu4HI
                                                                       bbvI
     aluI
     sacI
     bglAI
     bsp1286                 haeI
     banII    taqI           eaeI
     xhoI     salI mspI
     avaII    hincII mboII haeIII
     ecoRI tagI accI hpaII ballI aluI                                 mnlI
1    GAATTCTCGAGCTCGTCGACCGGAAGATGCCAGAGCTTTGTGTCCACTGCAAGCCCTCTCGGCTTCTGGAGTGGGGCTGCTCTTGGGACCTGTGC
     CTTAAGAGCTCGAGCAGCTGGCCTTCTACGGTCTCGAAACACAGGTGACGTTCGGGAGAGCCGAAGACCTCACCCCGACGAGAACCTGGAACACG
-31  linker            M  A  R  A  L  C  P  L  Q  A  L  W  L  L  E  W  V  L  L  G  P  C  A
                                        haeIII         bglI
                                        sau96I         sau96I
                                                       nlaIV
                                                       haeIII
                                  scrFI
                                  bstNI              fnu4HI
       mnlI                       aluI               bbvI
                                  fnu4HI
                                  bbvI hphI                       ecoO109I
101  TGCCCCCTCCAGCCTGGGCCTGAACCTGGACCGAGCTCAGCTCTATGCAGGCCAGCCAGTTGGATTTTCACTGACTTCCACAAG
     ACGGGGAGGTCGGACCCGGACTTGGACCTGGCTCGAGTCGAGATACGTCCGGTCGGTCAACCTAAAAGTGACTGAAGGTGTTC
-6   A  P  P  A  W  A  L  N  L  D  P  V  Q  L  T  F  Y  A  G  P  N  G  S  Q  F  S  L  D  F  H  K
         ↑
         H
                                               sau96I
                                               nlaIV
                                 hinPI         haeIII
                                 hhaI          sau96I
                                 nlaIV         nlaIV
                        bstXI    narI          ecoO109I bsp1286
                        haeIII   thaI          apaI     banII               mnlI
                        haeI     haeII         scrFI                        scrFI     mnlI
                        eaeI     banI          bstUI bstNI                            scrFI     haeIII
             nlaIII                ahaII saclI                              bstNI     fnu4HI    bstNI sau96I
             styI                                                                     bsp1286         mnlI
             ncoI
             ballI
201  GACAGCCATGGGAGAGTGGCCATCGTGGTGGGCGCCCCCAGCCAGGAGGAGACGGGGCCGGCGTGTTCCTGTGCCCCTGAGGGCCG
     CTGTCGGTACCCTCTCACCGGTAGCACCACCCGCGGGGGTCGGTCCTCCTCTGCCCCGGCCGCACAAGGACACGGGGACTCCCGGC
28   D  S  H  G  R  V  A  I  V  V  G  A  P  R  T  L  G  P  S  Q  E  E  T  G  G  V  F  L  C  P  W  R  A  E
```

```
                                                        seu3AI
                                                        mboI                                    bsp1286
                                          haeIII        dpnI                                    nlaIV         banI    aluI
                      rsaI                 eaeI   taqI  xhoII  alwI              hinPI                                
 801 CCAGAGTACTTCGACGGCTACTCGGGCCGTGGCCGTACTCGGGCGAGTTCGACGGGGATCTCAACACTACAGAATATGTCGCGTGCCCCACTTGA
     GGTCTCATGAAGCTGCCGATGAGCCCGGCACCGGCATGAGCCCGCTCAAGCTGCCCCTAGAGTTGTGATGTCTTATACAGCGCACGGGGTGAACCT
 228 P  E  Y  F  D  G  Y  W  G  Y  S  V  A  V  G  E  F  D  G  D  L  N  T  T  E  Y  V  V  G  A  P  T  W  S
                                                                                           bsmI alwNI
              scrPI                                                                        hgaI
              bstNI                                                     bstUI              ahaII
                                                                        hinPI
                                                                        hhaI
                                                                        bssHII
                                    fnu4HI                              fnu4HI
        sau96I                      bbvI                                bbvI sfaNI hhaI
        nlaIV          hinfI        mnlI alwNI
        avaII
 901 GCTGGACCCTGGAGAGCGGTGGAAATTTGGATTCTACTAGGAGGCTGCATCGGCTGCGGGCAGAGCAGATGGCGTCGTGTATTTGGGCATTCAGTGGC
     CGACCTGGGACCCTCGCCACCTTTAAACCTAAGATGATCCTCCGACGTAGCCGACGCCCGTCTCCAGCATAAACCCGTAAGTCACCG
 262 W  T  L  G  A  V  E  I  L  D  S  Y  Y  Q  R  L  H  R  L  R  A  E  Q  M  A  S  Y  F  G  H  S  V  A
                                                             scrFI
                                                             ncII
                        seu3AI                               mspI
                hincII  mboI                hinPI            hpaII                              haeIII
                ahaII   dpnI  nlaIII        hhaI                                                eaeI
             sstII foki mnlI            haeII
1001 TGTCACTGAGTCAACGGGATGGGAGGCATGATCTCGTGAGCTCCACTGTATATGGAGAGCCCGGACGAAACTGCCGAAGTGCCGAAGTGGGCGT
     ACAGTGACTCAGTTGCCCTACCCTCCGTACTAGAGCACTCGAGGTGACATATACCTCTCGGCCTGCTTTGACCGGCTTGACGGCTTCACCCGCA
 295 V  T  D  V  N  G  D  G  R  H  D  L  L  V  G  A  P  L  Y  M  E  S  R  A  D  R  K  L  A  E  V  G  R
                        seu96I
                        nlaIV
                        ecoO109I     hinPI
                        thaI haeIII  hhaI                              bsp1286
        fnu4HI mnlI                  thaI             bstUI            nlaIV
        bbvI fnu4HI     pflMI        banI    mnlI    aluI    hinfI
   pstI fnu4HI
1101 GTGTATTGTTCTCCAGCCGGAGGCCCCCACCCGCTGGTGCCCCAGCCTCCTGCTGACTGGCACACAGTCTATGGGCGATTCGGCTGCCATCG
     CACATAAACAAGAGGTCGGCCTCCGGGGGTGGGCGACCACGGACGACTGACGCTGTCTCAGATACCCGCTAAGCGACGAGACGGTAGC
 328 V  Y  L  F  L  Q  P  R  G  P  H  A  L  G  A  P  S  L  L  T  G  T  Q  L  Y  G  R  F  G  S  A  I  A
```

```
                                                               sau96I
                                                               haeIII sau96I
                                                               nlaIV bsp1286
                                                               banII hgiAI       apaI
                                                   bsp1286     ecoO109I
                                                               mnlI
        hgiAI        tth111I
        nlaIII       taqI                                                                          hphI
   xbaI fnu4HI bsp1286 mnlI                                                                        sau96I
  1 TCTAGAGCCGCCATGAGAGACACGTCCTCGACCACGTCCTCTGGGCGACTGTGCTGGCACTGGCTGTGTTGGAGTAGGAGGGCCCAACA      haeIII
    AGATCTCGGCGGTACTCTCTGTGCAGGAGCTGGTGCAGGAGACCCGCTGACACGACCGTGACCGACAACTTCATCCTCCCGGGTTGT
-26   M  R  A  R  P  R  P  L  W  A  T  V  L  A  L  A  G  V  G  P  N  I ↓ aluI
            mnlI      sacI                    hgiAI      sau96I
            thaI      hgiAI                   bsp1286    haeIII
   rsaI bstUI       bsp1286                    scrFI             ecoO109I     mnlI
                    banII          bstNI              mnlI                       mnlI
                     alwNI      bsp1286                                              ddeI
                               banII nlaIII bstNI
 101 TCTGTACCACGGCGAGGTGTGAGCTGCCAGCAGTGCCTGTGAGCCCATGTGTGCCTGTGCTGTGAGACCGAGAGACCGAGTGGAGC
     AGACATGGTGCCGCTCCACACTCGACGGTCGTCACGGACCGACACGAGACTCGGGGTACACACGGACACTCGGGAGACCCTCACCTCG
  5  C  T  T  R  G  V  S  S  C  Q  Q  C  L  A  V  S  P  M  C  A  W  C  S  D  E  A  L  P  L  G  S  P  P  R avaI              mnlI
                                                         sau96I     scaI  mnlI  ecoO109I
                                                         haeIII            rsaI
                                          hinfI     bsp1286 hinfI taqI        mnlI
 201 CTGTGACCTGAAGGAGAATCTGCTGAAGGATAACTGTGCCCAGAATCCATCGAGTTCCCAGTGAGTTCCACTCAGGACAGGCCCCTCAGC
     GACACTGGACTTCCTCTTAGACGACTTCCTATTGACACGGGTCTTAGGTAGCTCAAGGGTCACTCAAGGTGAGTCCTGTCCGGGGAGTCG
 38  C  D  L  K  E  N  L  L  K  D  N  C  A  P  E  S  I  E  F  P  V  S  E  A  R  V  L  E  D  R  P  L  S xmnI
                                                                                mboII
                                                                eaeI            taqI
                                                           nlaIV haeIII
                                                          mspI mspI       asuII
                                                          hpaII hpaII    hinfI       fokI
 301 GACAAGGGCTCTGGAGACAGCTCTCAAGTCACTCAAGTCAGTCCCCAGAGGATTGCACTCCGGCCAGATGATTCGAAGAATTTCTCATCCAAG
     CTGTTCCCGAGACCTCTGTCGAGAGTTCAGTGAGTTCAGTCAGGGGTCTCCTAACGTGAGGCCGGTCTACTAAGCTTCTTAAAGAGTAGGTTC
 71  D  K  G  S  G  D  S  S  Q  V  T  Q  V  S  P  Q  R  I  A  L  R  P  D  D  S  K  N  F  S  I  Q  V
              bsp1286
              banII     aluI bstNI
                          scrFI
```

Fig.2(b)

```
                                                                            rsaI
                                                                            nlaIV
                                                                            kpnI
                                                                            banI
                                                    alwNI                   scrFI
                                             sau3AI pflMI
                                             mboI   fokI
                                    nlaIII   fokI dpnI sfaNI                bstNI  aluI
       bspMI  mnlI  sau96I
       fnu4HI       avaII
401 TGCGGCAGTGAGGTGGAGGATTACCCTGTGACATCTACTACTTGATGGACCTGTCTTACTCCATGAAGGAGATGATCGTGGAGCATCCAGAACCTGGGTACCAA
    ACGCCGTCACTCCACCTCCTAATGGGACACTGTAGATGATGAACTACCTGGACAGAATGAGGTACTTCCTCTACTAGCAGCTCGTAGGTCTTGACCCATGGTT
105  R  Q  V  E  D  Y  P  V  D  I  Y  Y  L  M  D  L  S  Y  S  M  K  D  D  L  W  S  I  Q  N  L  G  T  K haeIII
       haeI                                 hphI
       eaeI            balI  sfaNI  aluI                                           nlaIII
501 GCTGGCCACCCAGATGCGAAAGCTCACCAGTAACCTGCGGATTGGCTTCGGGGCATTTGTGGACAAGCCTGTCACCATACATGTATATCTCCCACCA
    CGACCGGTGGGTCTACGCTTTCGAGTGGTCATTGGACGCCTAACGAAGCCCCGTAAACACCTGTTCGGACACAGTGGTATGTACATATAGAGGGGTGGT
138  L  A  T  Q  M  R  K  L  T  S  N  L  R  I  G  F  G  A  F  V  D  K  P  V  S  P  Y  M  Y  I  S  P  P hphI
                                                                            bstEII
                           mboII bspMI    nlaIII                            scrFI  bstNI
       sau96I              mnlI mnlI                 hgaI
       haeIII              mnlI                      nlaIII
       taqI
       ecoO109I
601 GAGGCCCTCGAAAACCCTGCTATGATATGAAGACCACCTGCTTGCCCATGTTTGGCTACAAACACGTGTGACGGCTAACTGACCAGTGACCCGCTTCA
    CTCCGGGAGCTTTTGGGACGATACTATACTTCTGGTGGACGAACGGGTACAAACCGATGTTTGTGCACACTGCCGATTGACTGGTCACTGGGCGAAGT
171  E  A  L  E  N  P  C  Y  D  M  K  T  T  C  L  P  M  F  G  Y  K  H  V  L  T  D  Q  V  T  R  F  N mnlI
                     mnlI  mboII nlaIV  sfaNI pflMI
701 ATGAGGAAGCAGAAGCAGAGTGTCACGGACAGTCCATGATGCCATACGAGGCTGCCTTTGATCATGCAGGCTACAGTCTGTGATGAAAGATTGG
    TACTCCTTCACTCTTCGTCTCACACAGTGCCTGTCAGGTACTACGGTATGCTCCGACGGAAACTACTACGTCCGATGTCAGACACTACTTTCTAACC
205  E  E  V  K  K  Q  S  V  S  R  N  R  D  A  P  E  G  G  F  D  A  I  M  Q  A  T  V  C  D  E  K  I  G fokI
       sfaNI
       nsiI
       avaII                                                    pleI
       mnlI  sfaNI  pflMI                              sfaNI    hinfI
                                                                                        mnlI
                                     nlaIII                                      ddeI   aluI
                         mnlI                                            nlaIII
                         bstXI ncoI                                      styI
801 CTGGAGGAATGATGCATCCCACTGCTGTGTTACCACTGATGCCAAGACTCATATAGCAATTGGACGGAAGGCTGGCAGGCATTGTCCAGCTAATGAC
    GACCTCCTTACTACGTAGGGTGACGACACAATGGTGACTACGGTTCTGAGTATATCGTTAACCTGCCTTCCGACCGTCCGTAACAGGTCGATTACTG
238  W  R  N  D  A  S  H  L  V  F  T  T  D  A  K  T  H  I  A  L  D  G  R  L  A  G  I  V  Q  P  N  D nlaIII
                 mnlI
901 GGGCAGTGTCATGTTGGTAGTGACAATTACTCTGCCTCACTCCACTACCATGGATTATCCCTCTTTGGGCTGATGACTGAGAAGCTATCCAGAAAACA
    CCCGTCACAGTACAACCATCACTGTTAATGATGAGACGGAGTGAGGTGATGGTACCTAATAGGGAGAAACCCGACTACTGACTCTTCGATAGGTCTTTTGT
271  G  Q  C  H  V  G  S  D  N  H  Y  S  A  S  T  T  M  D  Y  P  S  L  G  L  M  T  E  K  L  S  Q  K  N  I
```

Fig.2(c)

```
                                                      sau96I
                                                      avaII
                                                       scrFI
                                    aluI          hglAI   bstNI              nlaIII
                                    sacI foKI nlaIV     bsp1286               styI
                                                         banII                ncoI hinfI
1001 TCAATTGATCTTTGCAGTGACTGAATGACTGAATGAACTATAGTAGTGAGCTCATCCCAGGACCACAGTTGGGGTTCTGTCATGGATTC
     AGTTAACTAGAAACGTCACTGACTTTACATCAGTTAGATATCTTGATATCATCGAGTAGGGTCCTGGTGTCAACCCAAGACAGTACCTAAG
 305   N  L  I  F  A  V  T  E  N  V  V  N  L  T  Q  N  Y  S  E  L  I  P  G  T  T  V  G  V  L  S  M  D  S
                                                                 mboII
                                     mnlI aluI   sfaNI                    aluI       mnlI               styI
1101 CAGGAATGTCCTCAGTCATTGTGATGCTATGGGAAAATCCGTTCTAAGTAGAGCTCGAAGTGCCTGACCTCGAAGTTCTACGACTACTCTC
     GTCGTTACAGGAGTCAGTAACACTACGATACCCTTTTAGGCAAGATTTCATCTCGAGCTTCACGGACTGGAGGACTTCTCAACAGATAGGAAG
 338   S  N  V  L  Q  L  I  V  D  A  Y  G  K  I  R  S  K  V  E  L  E  V  R  D  L  P  E  E  L  S  L  S  F
                          haeIII                                                              haeIII
                          scrFI                                                                 haeI
                           bstNI             mnlI           pleI                  hphI         mnlI
                 mnlI     mnlI foKI haeI                    hinfI       aluI       bstEII
             bspMI
1201 AATGCCACTGCTCAACAATGAGGAGAGTCCTCAAGTCTTGTATGGGACTTCAAGATTGGAGACACGGGTGAGCTTCAGCATTGAGGCCAAGTGC
     TTACGGTGGACGAGTTGTTACTCCTCTCAGGAGTTCAGAACATACCCTGAAGTTCTAACCTCTGTGCCACTCGAAGTGTAACTCCGGTTCACG
 371   N  A  T  C  L  N  N  E  V  I  P  G  L  K  S  C  M  G  L  K  I  G  D  T  V  S  F  S  I  E  A  K  V  R
                                                                                   sau3AI
                                               scrFI                                mboI
             mnlI                             bstNI                                  dpnI     bstNI           bglI
1301 GAGGCTGTCCCCAGGAGAAGGAGAAGTCCTTACCATAAAGCCCGTGGGCTTCAAGGACAGCCCTGGATCGTCCAGTGCCACCTTGATTGTGACTGTGCCTG
     CTCCGACAGGGGTCCTCTTCCTCTTCAGGAATGGTATTTCGGGCACCCGAAGTTCCTGTCGGGACCTAGCAGGTCACGGTGGAAACTAACTGACACGGAC
 405   G  C  P  Q  E  E  K  E  K  S  F  T  I  K  P  V  G  F  K  D  S  L  I  V  Q  V  T  F  D  C  D  C  A  C
                                                                                              sau3AI
                                        ppuMI                                                  mboI
                   sau96I                nlaIV                                                  dpnI      bamHI
                   haeIII      fnu4HI    ecoO109I                                               alwI      alwI
         scrFI              bbvI                                                                xboII
         bstNI   aluI                                                                           nlaIV
1401 CCAGGCCCAAGCTTCGACTTGAATCTGTGTTACCGTGTTACCGGATTATCGTGATTATGGGACTTGAGTGTGGGTATGCCGTTGAGTGTGGGCTGGATCCCAG
     GGTCCGGGTTCGAAGCTTGAACATTGGATTATAGCAACAATGCCTAATAGCACTAATACCCTGAACTCACACCCATACGGCAACTCACACCCGACCTAGGGTC
 438   Q  A  Q  A  E  P  N  S  H  R  C  N  N  G  T  F  E  C  G  V  C  R  C  G  P  G  W  L  G  S  Q
```

Fig.2(d)

[Figure: DNA sequence with restriction enzyme annotations, nucleotides 1501–1980, with corresponding amino acid translation from residue 471 to 605.]

Fig.2(e)

```
            msel                          sfaNI
            aflII                         fokI                           tth111I
     pleI   aluI        bsrI              rsaI              fokI         hinfI scaI
     hinfI                                                  mnlI                     rsaI
2001 CGAGATTGAGTCAGTGAAAGAGCTAAGGACACTGGCAAGGATGCAGTGAATTGTACCTATAAGAATGAGGATGACTGTCGTCAGATTCCAGTACTAT
     GCTCTAACTCAGTCACTTTCTCGATTCCTGTGACCGTTCCTACGTCACTTAACATGGATATTCTTACTCCTACTGACACAGCAGTCTAAGGTCATGATA
 638  E  I  E  S  V  K  E  L  K  D  T  G  K  D  A  V  N  C  T  Y  K  N  E  D  D  C  V  V  R  F  Q  Y  Y sau96I
                                              haeIII
                                              sau96I
                                              nlaIV
                                                          ecoO109I                 ddeI
                                                          bspl286                  sau3AI
                                                          banII                    mboI
                                                   apaI                            dpnI          aluI   mseI
                                                   ecoO109I                        xhoII         bglII  hindIII
            hinfI         fokI          mboII      styI                                                 
            mboII
2101 GAAGATTCTAGTGGAAAGTCCATCCTGTATGTGGTAGAAGAGCCAGAGTGTCCCAAGGGCCCTGACTGATGAGATCTAAGCTT
     CTTCTAAGATCACCTTTCAGGTAGGACATACACCATCTTCTCGGTCTCACAGGGTTCCCGGGACTGACTACTCTAGATTCGAA
 671  E  D  S  S  G  K  S  I  L  Y  V  V  E  E  P  E  C  P  K  G  P  D  D
```

Fig. 3.

```
           XbaI
    EcoRI
synthetic  GAATTCTAGAGAGCCGCCATGAGAGCACGTCCTCGACCAGTCTCGGGCTGGCGACGTGGAGCTCTGGCTGTGTTGGAGTAGGAGGGCCC
           *  ***  ****  *** ** **** ** *********** ** ****** *********** ** *** **********
natural    CGCCGGGAGCCGGACGAGATGCGAGCCGGCCCCGGCCCCCGGGCCCTCGGGCCGACTGTGGCTGGGCGTTGGCTAGGAGGGCCC
           10        20        30        40        50        60        70        80        90        100
                                                                                              ApaI
            M  R  A  R  P  R  P  L  W  A  T  V  L  G  A  L  A  G  V  G  G  P
            10        20        30        40        50        60        70        80        90        100
```

HOST CELLS AND METHOD OF PRODUCING SOLUBLE ANALOGUES OF INTEGRINS

CROSS REFERENCES

This application is a divisional of U.S. application Ser. No. 08/380,227 filed 30 Jan. 1995, now abandoned which application is a continuation of U.S. application Ser. No. 08/218,878 filed 28 Mar. 1994 (abandoned), which application is a continuation of U.S. application Ser. No. 07/821,337 filed 13 Jan. 1992 (abandoned), which application is a continuation of U.S. application Ser. No. 07/444,490 filed 1 Dec. 1989 (abandoned), which application is a continuation-in-part of U.S. application Ser. No. 07/290,224 filed 22 Dec. 1988 (abandoned), which applications are incorporated herein by reference and to which applications priority is claimed under 35 USC§120.

BACKGROUND OF THE INVENTION

This invention is concerned with the preparation of complex soluble receptors. In particular it is directed to the synthesis of recombinant receptors for cell matrix or plasma proteins.

Cellular membranes contain polypeptides which are lodged in the lipid bilayer. Such polypeptides contain a domain which anchors the protein in the cell membrane, a hydrophobic transmembrane domain, together in many instances with a C-terminal cytoplasmic sequence. In general, these polypeptides are single chain molecules or are multiple chain molecules derived from an ancestral single chain expression product by post-translational proteolytic processing. Such multiple chain polypeptides usually are covalently linked by disulfide bonds. However, some of these polypeptides are noncovalently associated with one another by salt Bridges, Van der Waals forces, hydrophobic interactions and the like, and in such cases this association of polypeptide subunits into a larger aggregate is a prerequisite for biological activity.

The biological activity of such membrane-bound, multiple subunit molecules is varied, but in general reflects a receptor or binding function. Receptors serve to signal the cell regarding a condition or substance in the exterior environment of the cell, they serve to internalize an extracellular substance, or they function to attach cells to one another, to extracellular matrix substances, cell surface or plasma proteins.

A further subclass of membrane bound multiple subunit polypeptides are those in which each subunit is different, i.e. is not substantially homologous, and is encoded by a discrete gene. Such polypeptides are termed "MSP" (multiple subunit polypeptides) for the purposes of this invention. Numerous examples of such polypeptides or receptors are known, but the most substantial group is the class of cell surface receptors for extracellular matrix molecules, some of which have currently been identified and DNA encoding them cloned (see for example, Buck et al., "Ann. Rev. Cell Biol." 3:179 [1987] and Ruoslahti et al., "Science" 238: 491 [1987].)

Of particular interest is the platelet glycoprotein IIb-IIIa, a platelet membrane-bound receptor involved in platelet aggregation and which binds to fibrinogen, fibronectin, vitronectin and yon Willebrand factor. The two subunits constituting this receptor have been cloned (Fitzgerald et al. "Biochemistry" 26:8158 [1987] and Fitzgerald et al. "J. Biol. Chem." 262(9):3936 [1987]). Bennett et al. reported expression of the GPIIB subunit in Cos-1 cells, but the subunit was not found on the cell membrane (AHA 61st Scientific Sessions, Nov. 15, 1988). Bennett et al. suggested that membrane localization might require the formation of the IIb-IIIa complex. There was no teaching or suggestion that a recombinant, membrane-bound GPIIb-IIIa, even if it could be made, would bind to its proper ligands, e.g., fibrinogen. In addition, an oral disclosure by Frelinger et al. at the same meeting purported to describe the transient expression of full length GPIIb-IIIa on an unidentified recombinant cell surface; no other information was provided relating to the manner in which expression was allegedly obtained.

Corbi et al. orally reported the transient expression of functional full length LFA-1 in COS cells in September 1988 at the Titisee Symposium sponsored by Boehringer Ingelheim.

Membrane-bound MSPs present difficulties in purification and stability since the hydrophobic domains tend to induce the MSPs to micelles or aggregates. A form of these receptors is needed that is soluble, particularly in body fluids such as blood and in pharmacological excipients such as saline, without forming multiple molecular aggregates beyond proper heterodimer assembly. Accordingly, it is an object herein to synthesize such MSP forms.

It is another object to produce soluble forms of the GPIIb-IIIa receptor which are capable of properly binding their normal ligands.

It is a further object to express GPIIIa in recombinant cell culture.

It is an additional object to produce high yields of GPIIb-IIIa from recombinant cell culture.

These and other objects will be apparent from consideration of this application as a whole.

SUMMARY

In accordance with this invention, a method is provided for the preparation of a secreted analogue of a cell membrane-bound multiple subunit polypeptide (MSP), each subunit of which is encoded by a discrete gene, comprising 1) introducing into the nucleic acid encoding each of the subunits a mutation encoding an amino acid sequence variant of the MSP that renders the MSP no longer capable of becoming lodged in a lipid bilayer, and 2) transfecting a host cell with the nucleic acid of step 1, 3) culturing the host cell of step 2 and 4) recovering from the host cell culture biologically active soluble MSP. Also in accordance with this invention, nucleic acid and expression vectors are provided which encode an amino acid sequence variant of an integrin chain, in particular a variant in which the transmembrane domain of the integrin chain is modified so that it is no longer capable of becoming lodged in the cell membrane.

Also provided is a method for the preparation of GPIIb-IIIa comprising transforming a permissive host cell with nucleic acid encoding GPIIB-IIIa and culturing the host cell until GPIIb-IIIa accumulates in the cell membrane.

In specific embodiments, the objects of this invention are accomplished by providing a biologically active MSP amino acid sequence variant selected from the group consisting of (a) an MSP amino acid sequence variant having an inactivated membrane anchor domain and (b) a polypeptide comprising an MSP extracellular domain fused to the sequence of a polypeptide which is different from the MSP, this latter, for example, selected from an immunogen or a protein with a long plasma half life such as an immunoglobulin constant domain.

In another embodiment, MSP amino acid residues or carbohydrate substituents of MSPs or MSP analogues otherwise described herein are derivatized by covalent modification or are conjugated to nonproteinaceous polymers such as polyethylene glycol to produce an MSP derivative which exhibits improved circulatory half life.

In particular embodiments a polypeptide comprising a biologically active extracellular domain of an integrin is fused at its C-terminus to an immunoglobulin constant domain, or is linked to an immunogenic polypeptide.

The MSP variants provided herein are purified and formulated in pharmacologically acceptable vehicles for diagnostic or preparatory utility or in vivo use in the modulation of cell adhesion.

BRIEF DESCRIPTION OF THE DRAWINGS

Figure 1B:
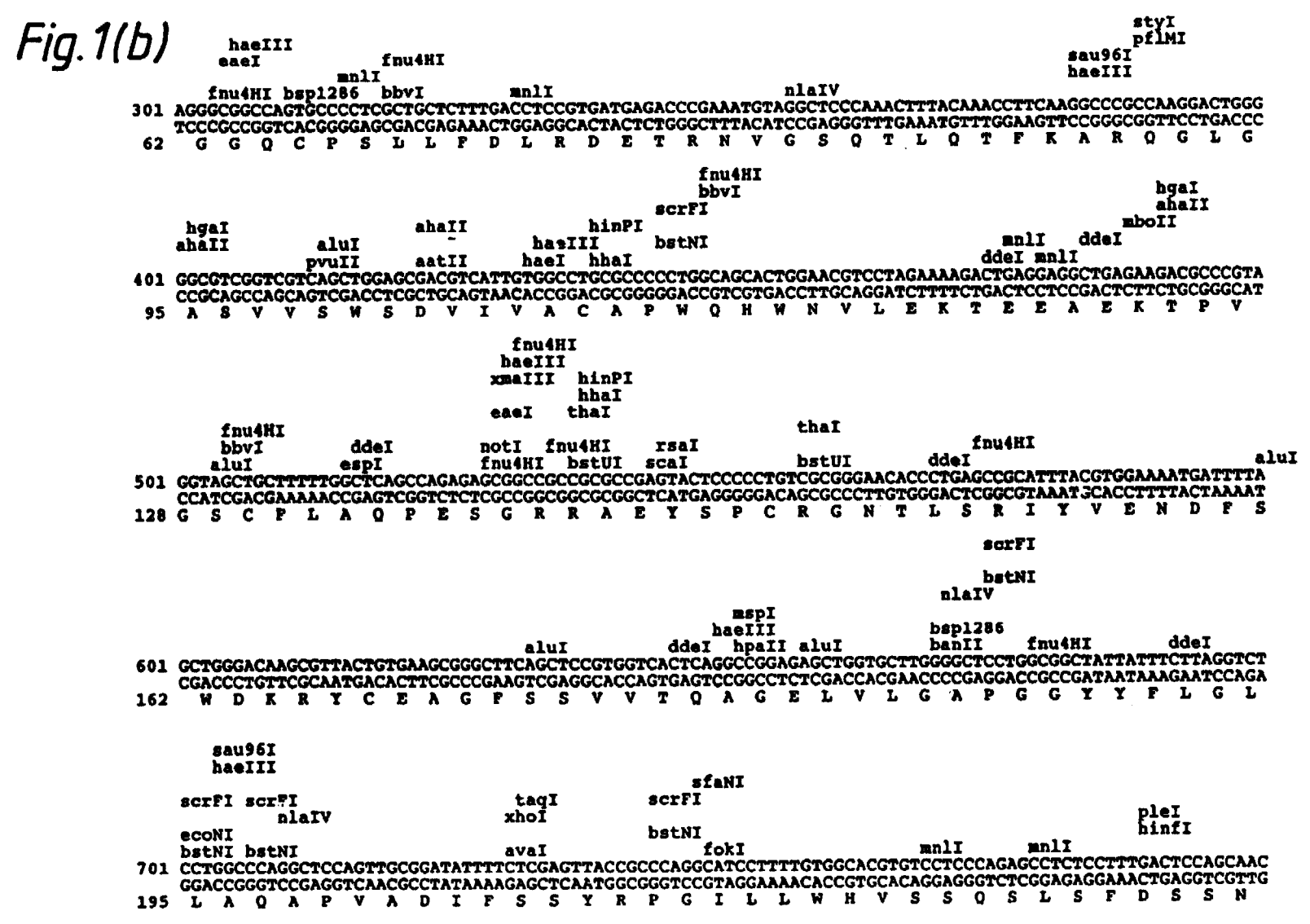
Figure 1D:
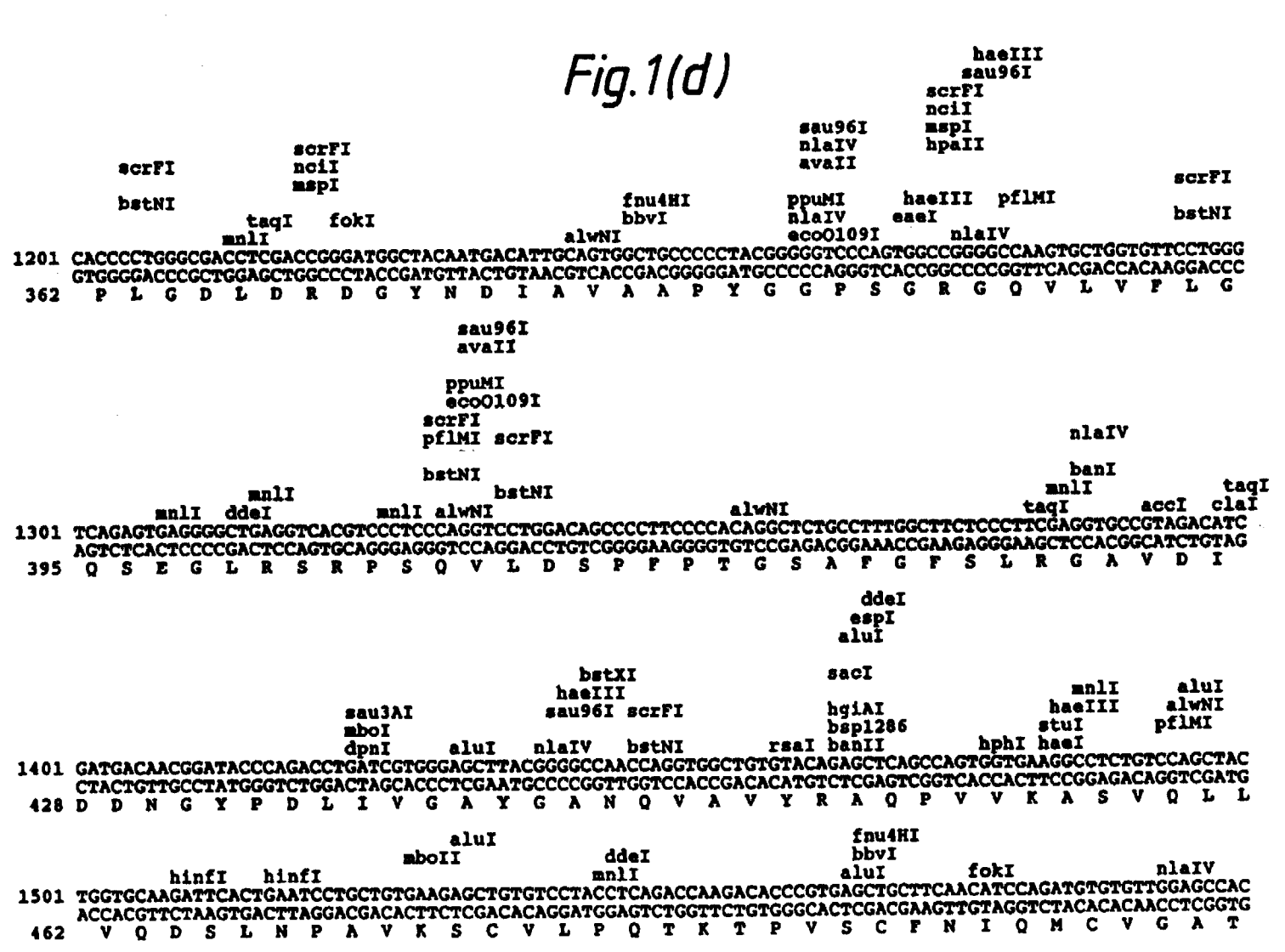
Figure 1E:
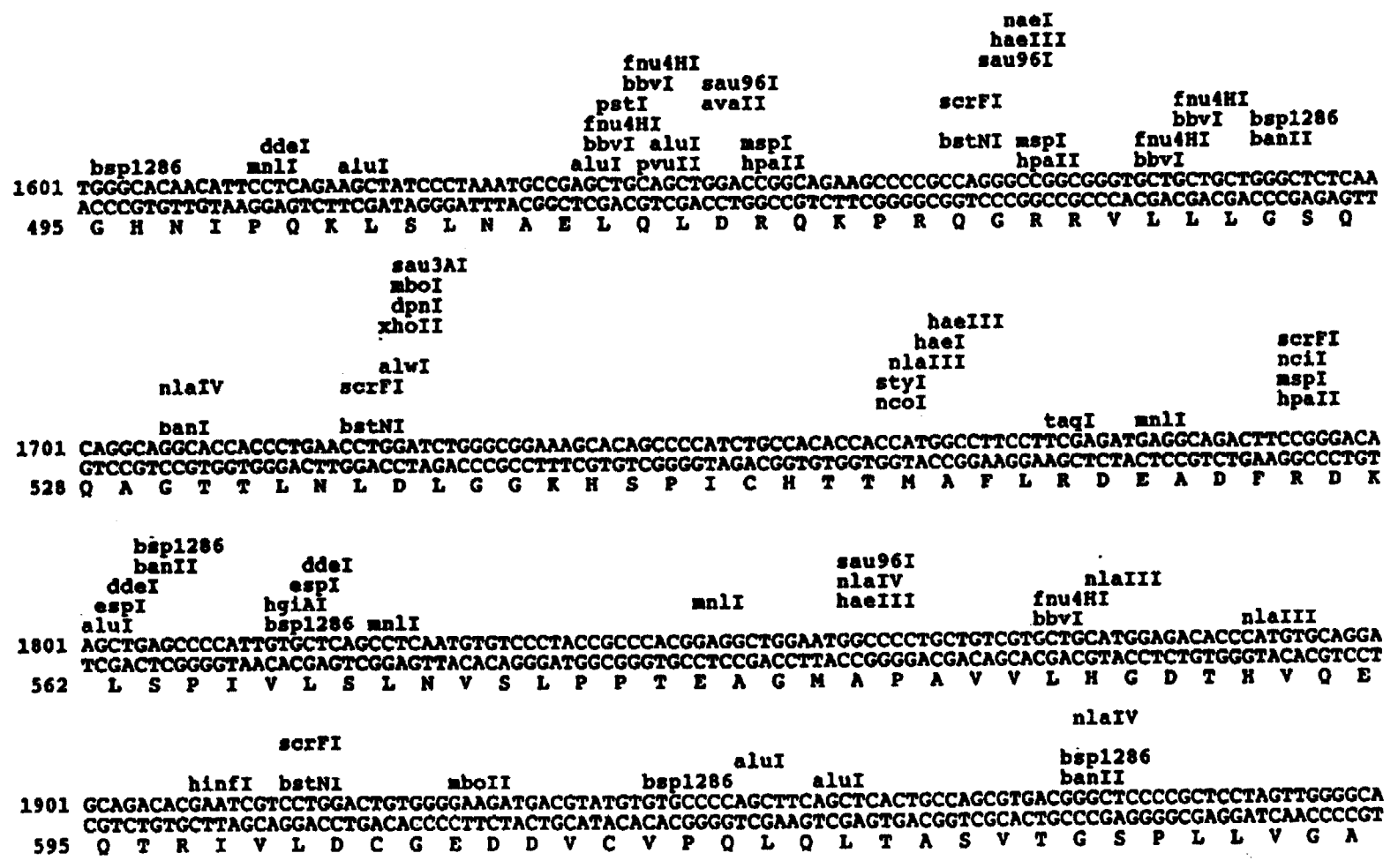
Figure 1F:
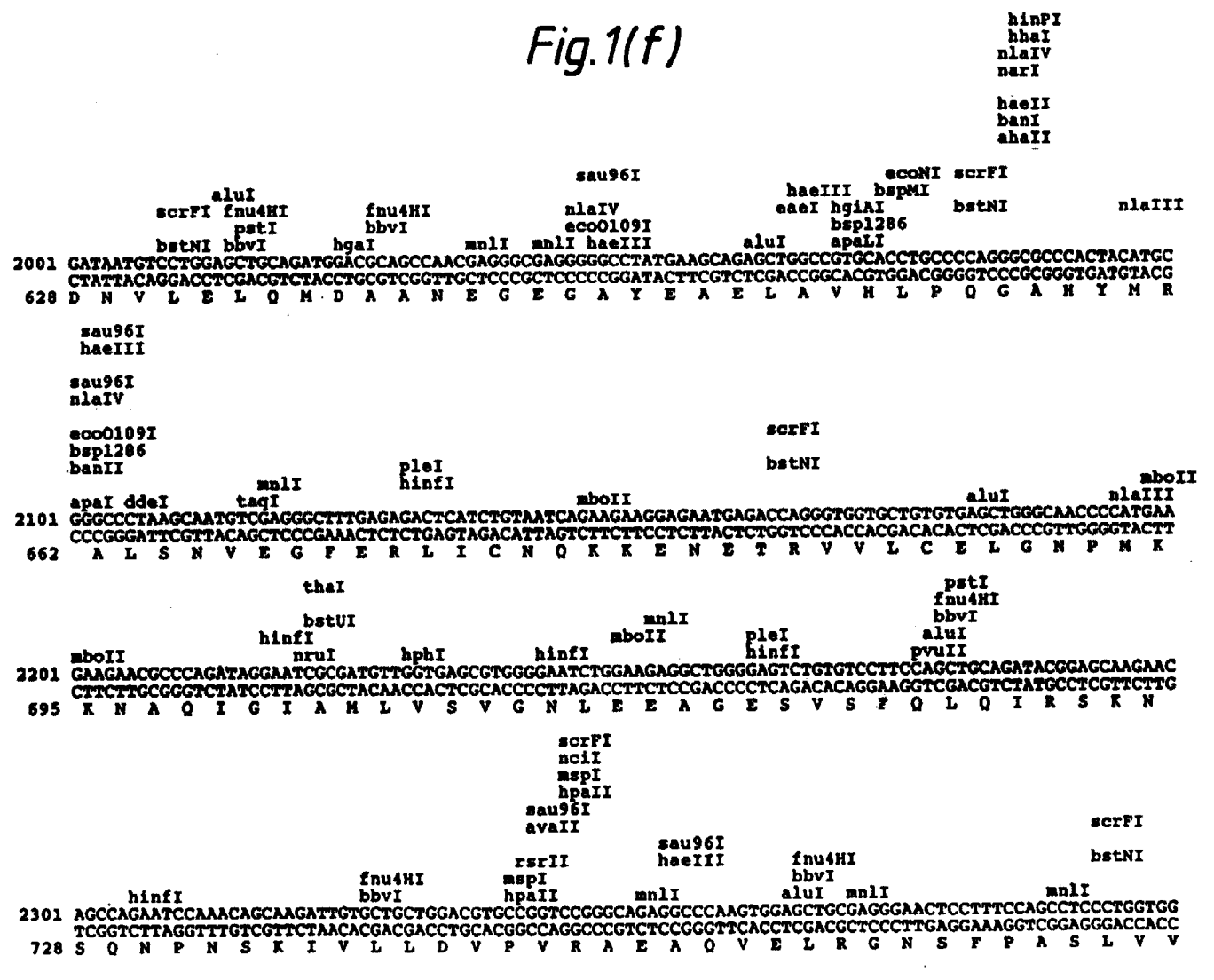
Figure 1G:
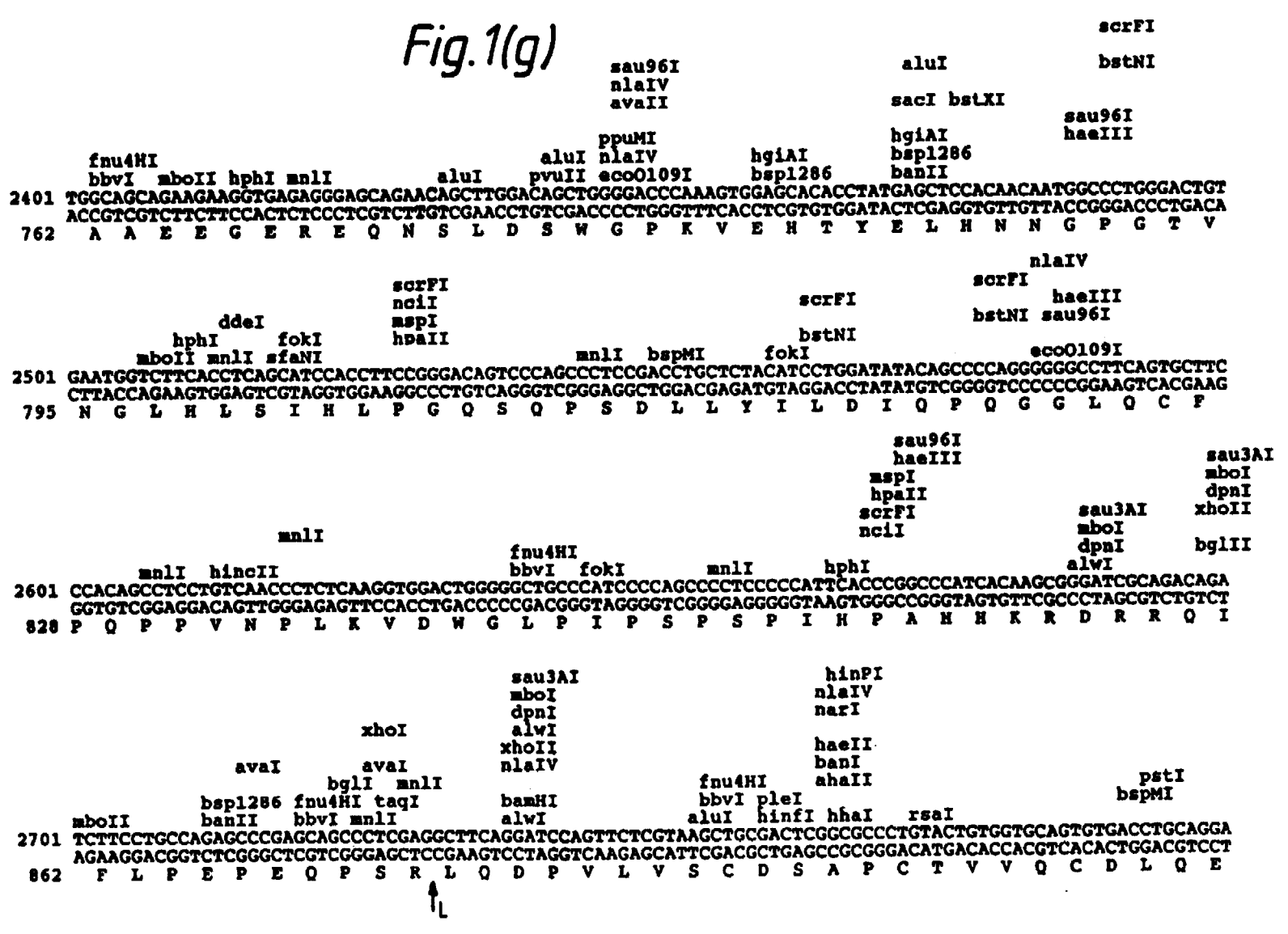
Figure 1H:
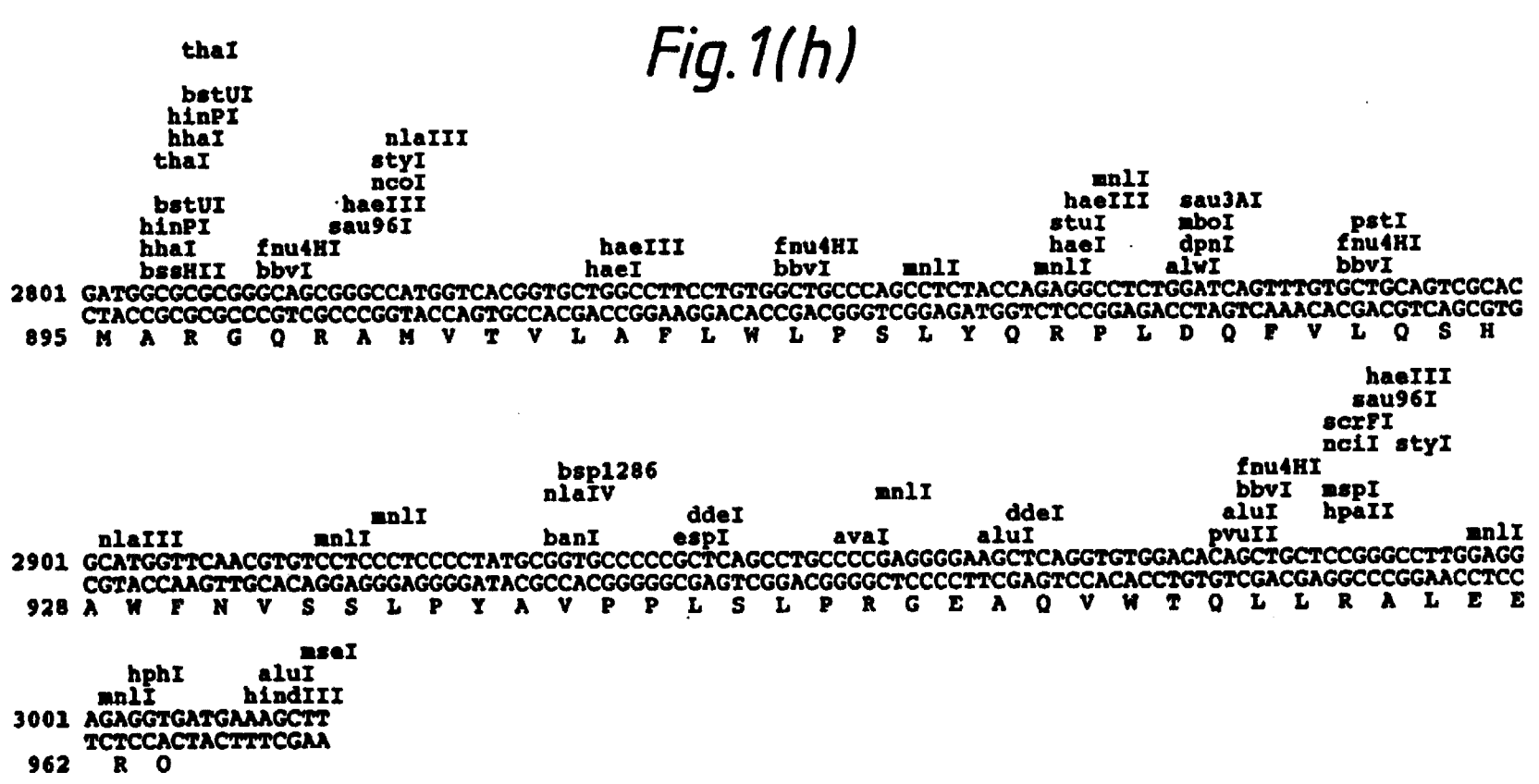

FIGS. 1(a)–(h) depict the amino acid (SEQ ID NO:2) and nucleotide sequence (SEQ ID NO:1) of a secreted form of the GPIIb subunit of the MSP GPIIb-IIIa. The signal processing site for the heavy and light forms of this subunit are designated, respectively, with arrow-H and arrow-L.

FIGS. 2(a)–(e) depict the amino acid (SEQ ID NO:4) and nucleotide sequence (SEQ ID NO:3) of a secreted form of the GPIIIa subunit of the MSP GPIIb-IIIa. The signal processing site is designated with an arrow.

FIG. 3 depicts a comparison of the native (natural) (SEQ ID NO:6) and redesigned (synthetic) (SEQ ID NO:5) nucleic acid sequences at the 5' end of the GPIIIa gene (Residues-26 through 2 of SEQ ID NO:2).

DETAILED DESCRIPTION

An MSP is defined herein to be a multichain polypeptide, at least one chain of which is ordinarily anchored in a cell membrane and at least two chains of which are discretely encoded. MSPs ordinarily contain at least two distinct chains, two of which are lodged directly in the cell membrane. One or more additional chains maybe covalently or noncovalently bound to the MSP chains ordinarily lodged in the cell membrane, but the additional chains may not themselves be anchored in the membrane. Such chains typically result from the post-translational processing of a single chain that becomes membrane anchored. Discretely encoded subunits are those which do not result from the posttranslational processing of a single translated protein, and their amino acid sequences are not homologous (i.e. the sequences of the subunits are not the same, and they do not assemble in nature into dimers or multimers of the same polypeptide). Instead, they are produced by the translation of independent mRNAs or polycistronic messages. Thus, the nucleic acids encoding MSP polypeptides ordinarily are found in nature under the control of different promoters and other transcription control sequences.

MSPs include principally cell surface receptors for extracellular matrix molecules, also defined as cellular adhesion receptors. Many of these receptors and their ligands, such ligands including the extracellular matrix molecules and plasma proteins such as fibrinogen as well as cell surface proteins such as I-CAM, are central to cellular adhesion phenomena involved in wound healing, morphogenic mobility, developmentally unrelated cellular migrations, hemostasis and metastasis. These cellular adhesion receptors are identified by functional and structural features. Functionally, they typically bind to polypeptides incorporating the sequence RGD, from which they are dissociated by competition with other polypeptides containing the RGD sequence such as the peptides RGDS or RGDV. Also, they frequently require a divalent cation such as calcium for ligand binding. MSPs may or may not include members of the immunoglobulin superfamily such as the T cell receptor. A group of MSPs involved in cell surface intracellular adhesive interactions have been designated integrins (see Buck et al., "Ann. Rev. Cell Biol." 3:179–205 [1987]).

Structurally, such cellular adhesion receptors belong to a supergene family of multimers in which a first single-chain polypeptide or disulfide cross-linked multi-chain polypeptide ($\alpha$-chain) is noncovalently associated with a second and different polypeptide (designated a $\beta$-chain), thereby forming a heteromultimer. The $\alpha$-chains of these receptors are quite diverse in terms of their amino acid sequence, and include the $\alpha$ subunit of avian integrin (band 1); $\alpha_1$, $\alpha_2$, and $\alpha_4$ of VLA1, 2 and 4, $\alpha_3$ of VLA 3 and avian integrin (band 2); $\alpha_F$ of VLA 5 and the fibronectin receptor; $\alpha_L$ of LFA-1, $\alpha_M$ of Mac-1, $\alpha_X$ of p150,95, $\alpha_H \alpha_L$ of GPIIb; and $\alpha_V$ of vitronectin. The $\beta$-chains typically fall into three classes, $\beta_1$ (avian integrin [band 3]; fibronectin receptor and VLA), $\beta_2$ (LFA-1/Mac-1; p150,95) and $\beta_3$ (GPIIb-IIIa and vitronectin receptor), the members of each $\beta$-class being substantially homologous or identical. It is preferred that the MSP selected contain the two (or more) chains which ordinarily associate with one another in nature since non-naturally occurring heteromers may not form complexes.

Each chain of an MSP is expressed in its native environment as a preprotein comprising a secretion signal which is processed during the extracellular orientation of the receptor. Also, at least one chain of each subunit will have a hydrophobic anchor containing a polypeptide sequence serving as a site for covalent addition of lipid, e.g. phospholipid, or a domain located in the C-terminal portion of the polypeptide and containing about from 10 to 30 predominantly hydrophobic residues such as phe, leu, ile, val, met, gly and ala. Such membrane anchoring sequences or domains will be collectively referred to herein as membrane anchor domains. A short hydrophilic cytoplasmic domain, on the order of 10 to 100 residues, usually is found C-terminal to transmembrane domains. The term subunit should be understood to mean polypeptide chain; it does not refer to domains or functional subregions of a given polypeptide chain.

Certain MSPs share other structural features, for example, wherein one subunit of the receptor contains cysteine-rich tandem amino acid sequence repeats in which greater than about 80% of the cysteine residues are alignable within about two residues of the cysteine residues of the tandem repeats of GPIIIa, wherein one subunit has the consensus N-terminal sequence Tyr/Phe/Leu-Asn-Leu-Asp (SEQ ID NO:7), or one subunit contains an amino acid domain having substantial sequence homology to the calmodulin calcium binding site.

Also included within the scope of HSPs are those receptors which are homologous to the above-described members of the integrin superfamily. Homologous, as defined herein, means having the sequence of a polypeptide of a member of the integrin superfamily which at least has substantially the same amino acid sequence homology to a known member of the superfamily as any presently known member has to any other known member. Typically, homologous means having greater than about 40% amino acid homology after aligning sequences for maximum homology, but not taking into account conservative substitutions.

This invention in part is based upon the discovery that discretely encoded MSPs, when modified to eliminate their ability to insert into the host cell membrane, nonetheless are fully assembled and secreted in biologically active form by recombinant host cells. Recombinant host cells secrete the subunits in correct association with one another such that the assembly exhibits the biological activity of the extracellular domain of the native MSP, despite the fact that proper association of the subunits is no longer facilitated by juxtaposition in the cell membrane. Further, proper assembly has been obtained even when the MSP sequences have not been fused to multimer-forming polypeptides, i.e. it has been found that MSPs will properly associate even without the aid of extraneous cross-linking polypeptides such as immunoglobulin chains.

Biological activity is defined in terms of the ability of the secreted MSP to qualitatively bind the ligand ordinarily bound by the MSP in its native environment, although it will be appreciated that the kinetics or other quantitative characteristics of ligand binding by the secreted MSP may vary from those of the native cell bound MSP. While secreted MSP most likely will retain many functional immune epitopes capable of cross-reacting with antibody raised against the native MSP, this alone is not enough for the secreted MSP to exhibit biological activity as defined herein; "biologically active" secreted MSP must exhibit the ability to bind to its ligand as well. However, it will be understood that not all MSP produced in accord with this invention need to exhibit biological activity in the sense defined here. Such biologically inactive but, for example, immunologically active MSP analogues find use in diagnostic assays, in raising antibodies against MSP, or in the purification of antibodies to MSP.

This invention is particularly concerned with amino acid sequence vahriants of MSPs. Amino acid sequence variants of MSPs are prepared with various objectives in mind, including increasing the affinity of the MSP for its binding partner, facilitating the stability, purification and preparation of the MSP (including enhanced water solubility and reduced membrane affinity), increasing its plasma half life, improving therapeutic efficacy as described above, introducing additional functionalities and lessening the severity or occurrence of side effects during therapeutic use of the MSP. Amino acid sequence variants of MSPs fall into one or a combination of the following classes: insertional, substitutional or deletional variants. Each MSP variant or analogue will have one inactivated membrane anchor domain, and this will be accomplished by insertion, substitution or deletion, but these variants optionally comprise additional mutations that are involved in other than inactivating the membrane anchor domain of one chain of the native MSP.

Insertional amino acid sequence variants are those in which one or more amino acid residues extraneous to the MSP are introduced into a predetermined site in the MSP including the C or N termini. Such variants are referred to as fusions of the MSP and a polypeptide containing a sequence which is other than that which is normally found in the MSP at the inserted position. Several groups of fusions are contemplated herein.

Immunologically active MSP fusions comprise an MSP and a polypeptide containing a non-MSP epitope. The non-MSP epitope is any immunologically competent polypeptide, i.e., any polypeptide which is capable of eliciting an immune response in the animal to which the fusion is to be administered or which is capable of being bound by an antibody raised against the non-MSP polypeptide. Typical non-MSP epitopes will be those which are borne by allergens, autoimmune epitopes, or other potent immunogens or antigens recognized by pre-existing antibodies in the fusion recipient, including bacterial polypeptides such as trpLE, beta-galactosidase, vital polypeptides such as herpes gD protein, and the like. Immunogenic fusions are produced by cross-linking in vitro or by recombinant cell culture transformed with DNA encoding an immunogenic polypeptide. It is preferable that the immunogenic fusion be one in which the immunogenic sequence is joined to or inserted into the MSP or fragment thereof by a peptide bond(s).

These products therefore consist of a linear polypeptide chain containing MSP epitopes and at least one epitope foreign to the MSP. It will be understood that it is within the scope of this invention to introduce the epitopes anywhere within the MSP molecule or fragment thereof. Such fusions are conveniently made in recombinant host cells or by the use of bifunctional cross-linking agents. The use of a cross-linking agent to fuse the MSP to the immunogenic polypeptide is not as desirable as a linear fusion because the cross-linked products are not as easily synthesized in structurally homogeneous form.

These immunogenic insertions are particularly useful when formulated into a pharmacologically acceptable carrier and administered to a subject in order to raise antibodies against the MSP, which antibodies in turn are useful in diagnostics or in purification of MSP by immunoaffinity techniques known per se. Alternatively, in the purification of MSPs, binding partners for the fused non-MSP polypeptide, e.g. antibodies, receptors or ligands, are used to adsorb the fusion from impure admixtures, after which the fusion is eluted and, if desired, the MSP is recovered from the fusion, e.g. by enzymatic cleavage.

Other fusions, which may or may not also be immunologically active, include fusions of the mature MSP sequence with a signal sequence heterologous to the MSP, fusions of transmembrane-modified MSPs (including sequence deletions or modifications so that the MSP could not lodge in the cell membrane), for example, to polypeptides having enhanced plasma half life (ordinarily >about 20 hours) such as immunoglobulin chains or fragments thereof which confer enhanced plasma half life.

Signal sequence fusions are employed in order to mare expeditiously direct the secretion of the MSP. The heterologous signal replaces the native MSP signal, and when the resulting fusion is recognized, i.e. processed and cleaved by the host cell, the MSP is secreted. Signals are selected based on the intended host cell, and may include bacterial yeast, mamalian and viral sequences. The native MSP signal or the herpes gD glycoprotein signal is suitable for use in mammalian expression systems.

Plasma proteins which have enhanced plasma half-life longer than that of soluble forms of MSPs having modified membrane anchor domains include serum albumin, immunoglobulins, apolipoproteins, and transferrin. Preferably, the MSP-plasma protein used for the fusion is not significantly immunogenic in the animal in which it is used (i.e., it is homologous to the therapeutic target) and the plasma protein does not cause undesirable side effects in patients by virtue of its normal biological activity.

In a specific embodiment the MSP extracellular domain is conjugated with an immunoglobulin constant region sequence. Immunoglobulins and certain variants thereof are known and many have been prepared in recombinant cell culture. For example, see U.S. Pat. No. 4,745,055, EP 256,654, Faulkner et al., Nature 298:286 (1982); EP 120, 694, EP 125,023, Morrison, J. Immun. 123:793 (1979); Köhler et al., P.N.A.S. USA77:2197 (1980); Raso et al., Cancer Res. 41:2073 (1981); Morrison et al., Ann. Rev.

Immunol. 2:239 (1984); Morrison, Science 229:1202 (1985); Morrison et al., P.N.A.S. USA 81:6851 (1984); EP 255,694; EP 266,663, and WO 88/03559. Reassorted immunoglobulin chains also are known. See for example U.S. Pat. No. 4,444,878, WO 88/03565, and EP 68,763 and references cited therein. See also Gascoigne et al., P.N.A.S. USA 84:2936-2940 (May, 1987), EP 325,224, and Thesis of Andrew Scott Peterson (Harvard University; degree awarded Nov. 22, 1988).

Ordinarily, the extracellular domains of MSPs are fused C-terminally to the N-terminus of the constant region of an immunoglobulin in place of the variable region(s) thereof, retaining at least functionally active hinge, CH2 and CH3 domains of the constant region of an immunoglobulin heavy chain. Two forms of such fusions are embraced herein. In one, the extracellular domains of two or more ordinarily membrane-bound MSP chains are fused N or C terminally to immunoglobulin constant regions (heterofusion), while in the other form only one chain of the MSP is fused to a constant region (monofusion). The heterofusions include fusions with either light or heavy chain constant regions, or both. The heterofusion is produced by transforming a host cell with DNA encoding the light chain fusions, the heavy chain fusions or both. For example, transfection with DNA encoding one MSP chain fused to a heavy chain constant region and the other MSP chain fused to a light chain constant region will result in heterotetramers or heterodimers bearing light and heavy chain fusions with MSP chains. These are not as desirable as monofusions since they are not as likely to be biologically active. Note that monofusions may contain more than one fused chain, but in these cases the MSP chain will always originate with the same subunit.

Monofusions are immunoglobulin variants in which one chain of an MSP is fused to a heavy or light chain (or constant domain thereof), while the remaining chain(s) of the MSP are not fused to an immunoglobulin but rather are associated with the fused chain in substantially the fashion as is normally the case with the native MSP. Typically, both the fused and unfused MSP chains in monofusions will be variants in which the membrane anchor domains are modified so as to not lodge in the membrane, most commonly where the membrane anchor domain of one MSP chain is deleted, and in the other the membrane anchor domain is deleted and then the remaining extracellular region fused at its N-terminus to the C-terminus of an immunoglobulin constant domain. The MSP chain or its fragment is fused to either a light chain or a heavy chain, but preferably a heavy chain. If the MSP only contained one membrane anchored chain then the remaining chain(s) will typically have their native sequence.

It may be desirable to produce mono-or polyfusions having immunoglobulin antigen binding capability as well as the capacity to bind the MSP ligand. Such products are made by transforming the host cells with DNA encoding light and heavy chain capable of binding an antigen (or are selected to already produce light chain) together with the light and/or heavy chain MSP fusion and the unfused MSP chain(s) (in the case of monofusions). This will yield constructs, for example, having the normal structures of immunoglobulins except that one or both light-heavy arms of the immunoglobulin will comprise a fusion with one chain of the MSP which in turn is assembled (covalently or noncovalently) with the remaining chain(s) of the MSP.

In those instances in which the fusion transformants also produce (or are transformed to produce) immunoglobulin chains not fused to an MSP subunit, the immunoglobulin variable domains may have unknown or known specificity for a given antigen. It is preferred that the host cells not be constitutively capable of making undetermined antibody, but rather that if they are to produce antibody that it be by transformation with DNA encoding a known immunoglobulin. Such immunoglobulin (which may include both heavy as well as light chains) exhibit specificity for a known antigen. Alternatively, these companion immunoglobulin chains will be devoid of functional variable or hypervariable domains (so as to be capable of multimer assembly but not antigen binding activity). For example, a product in MSP fusion secreted and recoverable from host cells capable expressing an intact head and light chain companion immunoglobulin will bear an antigen binding functionality as well as an MSP functionality. Such products will facilitate the crosslinking of MSP ligand with any desired antigen. Host cells may make more than one immunoglobulin product in such multiple transfomations, and accordingly it may be necessary to recover one multimer form from another. This however, will be a routine matter requiring separation on a gel or other chromatographic procedure, or by affinity chromatography based on the MSP ligand, the antigen or both.

Other proteins having extended plasma half life are fused to the MSP in similar fashion, except that instead of an immunoglobulin chain a transferrin, albumin, apolipoprotein or other sequence is employed. Monofusions are preferred when MSP chains are fused to single chain plasma proteins which do not ordinarily assemble into multimers.

The boundary for an MSP extracellular domain generally is at, or within about 20 residues N-terminal from, the N-terminus of the membrane anchor domain, and are readily identified from an inspection of the MSP sequence. It is not necessary to use the entire MSP extracellular domain, however, since smaller segments are commonly found to be adequate for ligand binding. Such segments are routinely identified by making deletional mutants or enzymatic digests and screening for ligand binding to identity active fragments, and fall within the scope of the term "MSP".

The MSP extracellular domain generally is fused at its C-terminus to the N-terminus of the immunoglobulin constant region or other stable plasma protein. The precise site at which the fusion is made is not critical; other sites neighboring or within the extracellular region or C-terminal to the mature N-terminus of the plasma protein may be selected in order to optimize the secretion or binding characteristics of the soluble MSP. The optimal site will be determined by routine experimentation.

Exemplary hereto-and chimeric MSP-immunoglobulin variants produced in accordance with this invention are schematically diagrammed below. "A" means at least a portion of the extracellular domain of an MSP containing its ligand binding site; $A_1$, $A_2$, $A_3$, etc. represent individual subunit chains of A; $V_L$, $V_H$, $C_L$ and $C_H$ represent light or heavy chain variable or constant domains of an immunoglobulin; n is an integer; and Y designates a covalent cross-linking moiety.

(a) $AC_L$;

(b) $AC_L$—$AC_L$;

(c) $AC_H$—[$AC_H$, $AC_L$—$AC_H$, $AC_L$—$V_HC_H$, $V_LC_L$—$AC_H$, or $V_LC_L$—$C_H$];

(d) $AC_LAC_H$—[$AC_H$, $AC_L$—$AC_H$, $AC_L$—$V_HC_H$, $V_LC_L$—$AC_H$, or $V_L C_L$—$V_HC_H$];

(e) $AC_L$—$V_HC_H$—[$AC_H$, $AC_L$—$AC_H$, $AC_L$—$V_HC_H$, or $V_LC_L$—$V_HC_H$];

(f) $V_LC_L$—$AC_H$[$AC_H$, $AC_L$—$AC_H$, $AC_L$—$V_HC_H$, $V_LC_L$—$AC_H$, or $V_LC_L$—$V_HC_H$]; or (g) $[A\text{—}Y]_n\text{—}[V_L C_L\text{—}V_H C_H]_2$.

The structures shown in this table show only key features, e.g. they do not show disulfide bonds. These are omitted in the interests of brevity. However, where such domains are required for binding activity they shall be construed as being present in the ordinary locations which they occupy in the immunoglobulin domain. These examples are representative of divalent antibodies; more complex structures would result by employing inmmunoglobulin heavy chain sequences from other classes, e.g. IgM. The immunoglobulin $V_L V_H$ antibody combining site, also designated as the companion immunoglobulin, preferably is capable of binding to a predetermined antigen.

Exemplary immunoglobulin constructs are described schematically below. Vertical lines indicate a noncovalent or covalent associative relationship.

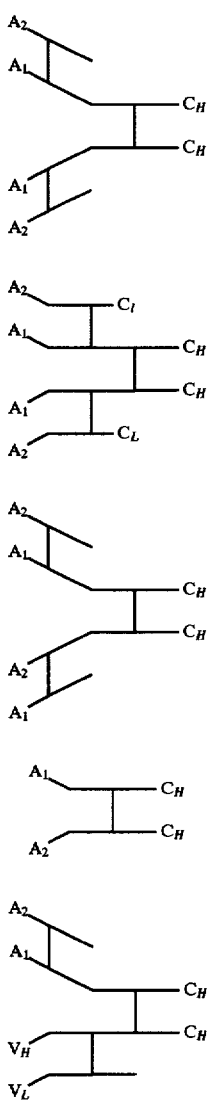

(h)

(i)

(j)

(k)

(l)

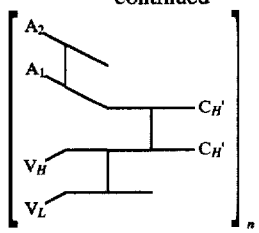

(m)

where n = 5 and $C_H'$ is the secreted heavy chain of IgM

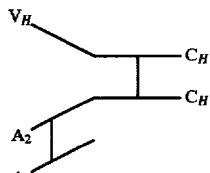

(n)

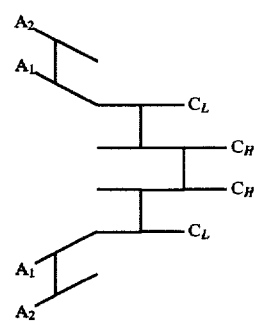

(o)

In product "(o)" the $C_H$ V domains have been deleted.

Suitable companion immunoglobulin combining sites and fusion partners are obtained from human IgG-1, -2, -3, or -4 subtypes, IgA, IgE, IgD or IgM, but preferably IgC-1. It is preferred to use the soluble form of IgM, or one in which the IgM membrane anchor domain has been modified so that it no longer lodges in the membrane.

A preferred embodiment is a fusion of an N-terminal portion of an MSP with a sequence beginning in the hinge region just upstream of the papain cleavage site which defines IgG $F_c$ chemically (residue 216, taking the first residue of heavy chain constant region to be 114 [Kabat et al., "Sequences of Proteins of Immunological Interest" 4th Ed., 1987], or analogous sites of other immunoglobulins).

The immunoglobulin or other plasma-stable polypeptide is fused to the C-termini of one or more of the MSP subunits, typically in place of at least one transmembrane and cytoplasmic domain of an MSP chain, although ordinarily only one of the subunits is substituted. In the case of GPIIb-IIIa this would Be the beta subunit. The immunoglobulin domain such as a heavy chain also can be associated in normal fashion with a truncated or intact immunoglobulin heavy chain.

Variants in which an MSP extracellular domain is substituted for the variable region of an immunoglobulin chain are believed to exhibit improved in vivo plasma half life. These chimeras are constructed in a fashion similar to chimeric antibodies in which a variable domain from an antibody of one species is substituted for the variable domain of another species. See, for example, EP 0 125 023, Munro, Nature 312: (13 Dec. 1984); Neuberger et al., Nature 312: (13 Dec.

1984); Sharon et al., Nature 309: (24 May 1984); Morrison et al., Proc. Natl. Acad. Sci. USA 81:6851–6855 (1984); Morrison et al. Science 229:1202–1207 (1985); and Boulianne et al., Nature 312:643–646 (13 Dec. 1984). The DNA encoding the MSP extracellular domain is cleaved by a restriction enzyme at or proximal to the 3' end of the DNA encoding the domain and at a point at or near the DNA encoding the N-terminal end of the mature MSP polypeptide (where use of a different leader is contemplated) or at or proximal to the N-terminal coding region for the MSP (where the native MSP signal is employed). This DNA fragment then is readily inserted into DNA encoding e.g. an immunoglobulin light or heavy chain constant region and, if necessary, tailored by deletional mutagenesis. Preferably, this is a human immunoglobulin. DNA encoding immunoglobulin light or heavy chain constant regions is known or readily available from cDNA libraries or is synthesized. See for example, Adams et al., Biochemistry 19:2711–2719 (1980); Cough et al., Biochemistry 19:2702–2710 (1980); Dolby et al., P.N.A.S. USA, 77:6027–6031 (1980); Rice et al., P.N.A.S. USA 79:7862–7865 (1982); Falkner et al., Nature 298:286–288 (1982); and Morrison et al., Ann. Rev. Immunol 2:239–256 (1984).

DNA encoding the chimeric chain(s) is transfected into a host cell for expression. If the host cell is producing an immunoglobulin prior to transfection then one need only transfect with the MSP fused to light or to heavy chain to produce a heteroantibody. The aforementioned immunoglobulins having one or more arms bearing the MSP domain and one or more arms bearing companion variable regions result in dual specificity for MSP ligand and for an antigen. These are produced by the above-described recombinant methods or by in vitro procedures. In the latter case, for example, $F(ab')_2$ fragments of the MSP fusion and an immunoglobulin are prepared, the $F(ab')_2$ fragments converted to Fab' fragments by reduction under mild reducing conditions, and then reoxidized in each other's presence under acidic conditions in accord with methods known per se. See also U.S. Pat. No. 4,444,878.

Additionally, procedures are known for producing intact heteroantibodies from immunoglobulins having different specificities. These procedures are adopted for the in vitro production of heterochimeric antibodies by simply substituting the MSP fusions for one of the previously employed immunoglobulins.

In an alternative method for producing a heterofunctional antibody, host cells producing an MSP-immunoglobulin fusion, e.g. transfected myelomas, also are fused with B cells or hybridomas which secrete antibody having the desired companion specificity for an antigen. Heterobifunctional antibody is recovered from the culture medium of such hybridomas, and thus maybe produced somewhat more conveniently than by conventional in vitro resorting methods (EP 68,763).

Another class of MSP variants are deletional variants. Deletions are characterized by the removal of one or more amino acid residues from an MSP sequence. Typically, the membrane anchor and cytoplasmic domains of all MSP subunits are deleted. However, any other suitable site N-terminal to the transmembrane which preserves the matrix protein or ligand-binding capability of the MSP is suitable. Excluded from the scope of deletional variants are the protein digestion fragments that may have heretofore been obtained in the course of elucidating amino acid sequences of MSPs.

Substitutional variants are those in which at least one residue in the MSP sequence has been removed and a different residue inserted in its place. Table 1 below describes substitutions which in general will result in fine modulation of the characteristics of an MSP.

TABLE 1

| Original Residue | Exemplary Substitutions |
|---|---|
| Ala | ser |
| Arg | lys |
| Asn | gln; his |
| Asp | glu |
| Cys | ser; ala |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in MSP properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteinyl or prolyl is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanyl, is substituted for (or by) one not having a side chain, e.g., glycyl.

A preferred class of substitutional or deletional variants are those involving a membrane anchor region of the MSP. Transmembrane regions of MSP subunits are highly hydrophobic or lipophilic domains that are the proper size to span the lipid bilayer of the cellular membrane. They are believed to anchor the MSP in the cell membrane. Other cell surface molecules are anchored by lipid modification, as by phospholipid anchors.

Deletion or substitution of the membrane anchor domain will facilitate recovery and provide a soluble form of the MSP by reducing its cellular or membrane lipid affinity and improving its water solubility. If the membrane anchor domains are deleted one avoids the introduction of potentially immunogenic epitopes, either by exposure of otherwise intracellular polypeptides that might be recognized by the body as foreign or by insertion of heterologous polypeptides that are potentially immunogenic. A principal advantage of the membrane anchor domain-deleted MSP is that it is secreted into the culture medium of recombinant hosts. This variant is soluble in body fluids such as blood and does not have an appreciable affinity for cell membrane lipids, thus considerably simplifying its recovery from recombinant cell culture. Surprisingly, MSPs in which membrane inserted chains have been modified so as to be no longer capable of stable insertion into cell membranes are capable of proper association and secretion from recombinant host cells even if the MSP chains are not fused to a multimer-forming sequence such as an immunoglobulin. A multimer-forming sequence is a multichain polypeptide that contains that portion of a multiple chain polypeptide that, when in the unfused form in nature, forms covalently or noncovalently associated multiple chain structures.

It will be amply apparent from the foregoing discussion that substitutions, deletions, insertions or any combination thereof are introduced to arrive at a final construct. None of the variants will have a functional membrane anchor domain and preferably will not have a functional cytoplasmic sequence. This is generally accomplished by deletion of the relevant domain, although adequate insertional or substitutional variants also are effective for this purpose. For example, the transmembrane domain is substituted by any amino acid sequence, e.g. a random or predetermined sequence of about 5 to 50 serine, threonine, lysine, arginine, glutamine, aspartic acid and like hydrophilic residues, which altogether exhibit a hydrophilic hydropathy profile. Like the deletional (truncated) MSPs, these variants are secreted into the culture medium of recombinant hosts.

MSP variants are prepared conveniently by site specific mutagenesis of nucleotides in the DNA encoding the MSP, thereby producing DNA encoding the variant, and thereafter expressing the DNA in recombinant cell culture. Obviously, changes in the DNA encoding the variant MSPs must not place the sequence out of reading frame and preferably will not create complementary regions that could produce secondary mRNA structure deleterious to expression (EP 75, 444A). The MSP variants typically exhibit the same matrix or ligand binding activity as does the naturally-occurring prototype, although variants also are selected in order to modify the characteristics of the MSP as indicated above.

While the site for introducing an amino acid sequence variation is predetermined, the mutation per se need not be predetermined. For example, in order to optimize the performance of a mutation at a given site, random or saturation mutagenesis (where all 20 possible residues are inserted) may be conducted at the target codon or region and the expressed MSP variants screened for the optimal combination of desired activities.

MSP variants that are not capable of binding to their matrix proteins or ligands are useful nonetheless as immunogens for raising antibodies to the MSP or as immunoassay kit components (labelled, as a competitive reagent for native MSP, or unlabelled as a standard for an MSP assay) so long as at least one MSP epitope remains active.

Contemplated herein are MSPs or MSP amino acid sequence or glycosylation variants (including those already described above) wherein one or more MSP subunits are conjugated with a nonproteinaceous polymer. It will be understood that the nonproteinaceous polymer which is conjugated to MSP excludes oligosaccharides that are present in the same positions in the native or starting MSP, i.e. the polymer is extraneous or heterologous to the MSP.

It is within the scope hereof to move, add or delete glycosylation sites by site-directed mutagenesis of MSP polypeptide in order to increase the number of or change the location of the carbohydrate substituents. The nature of the carbohydrate is modified in conventional fashion by in vitro enzymatic digestion or by selecting host cells that affix the selected carbohydrate (or do not glycosylate at all).

The nonproteinaceous polymer ordinarily is a hydrophilic synthetic polymer, i.e., a polymer not otherwise found in nature. However, polymers which exist in nature and are produced by recombinant or methods are useful, as are polymers which are isolated from nature. Hydrophilic polyvinyl polymers fall within the scope of this invention, e.g. polyvinylalcohol and polyvinylpyrrolidone. Particularly useful are polyalkylene ethers such as polyethylene glycol, polypropylene glycol, polyoxyethylene esters or methoxy polyethylene glycol; polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextran sulfate, dextran, dextrins, glycogen, or the polysaccharide subunit of acid mucopolysaccharides, e.g. hyaluronic acid; polymers of sugar alcohols such as polysorbitol and polymannitol; and heparin. Where the polysaccharide is the native glycosylation or the glycosylation attendant on recombinant expression of MSP, the site of substitution ordinarily is located at other than an N or O-linked glycosylation site of the MSP or the MSP variant is an amino acid sequence variant in which an additional or substitute N or O-inked site has been introduced into the molecule.

Mixtures of such polymers are employed, or the polymer may be homogeneous. The polymer prior to crosslinking need not be, but preferably is, water soluble, but the final conjugate must be soluble in biological fluids such as blood. In addition, for therapeutic uses the polymer should not be highly immunogenic when conjugated to the MSP, nor should it possess viscosity that is incompatible with intravenous infusion or injection if it is intended to be administered by such routes.

Preferably the polymer contains only a single group which is reactive with MSP. This helps to avoid crosslinking of MSP molecules. However, it is within the scope herein to optimize reaction conditions to reduce crosslinking, or to purify the reaction products through gel filtration or chromatographic sieves to recover substantially homogeneous derivatives.

The molecular weight of the polymer ranges about from 100 to 500,000, and preferably is about from 1,000 to 20,000. The molecular weight chosen will depend upon the nature of the polymer and the degree of substitution. In general, the greater the hydrophilicity of the polymer and the greater the degree of substitution, the lower the molecular weight that can be employed. Optimal molecular weights will be determined by routine experimentation. Ordinarily, the molecular weight of the MSP-polymer conjugate will exceed about 70,000 although molecules having lesser molecular weights are suitable.

The polymer generally is covalently linked to MSP through a multifunctional crosslinking agent which reacts with the polymer and one or more amino acid or sugar residues of MSP. However, it is within the scope of this invention to directly crosslink the polymer to the MSP by reacting a derivatized polymer with MSP, or vice versa.

A suitable MSP covalent crosslinking site is the N-terminal amino group and epsilon amino groups found on lysine residues, although other amino, imino, carboxyl, sulfuryl, hydroxyl or other hydrophilic groups serve as useful sites of substitution. The polymer may be covalently bonded directly to MSP without the use of a multifunctional (ordinarily bifunctional) crosslinking agent. Examples of such crosslinking agents include 1,1-bis(diazoacetyl)-2-phenylethane, glutaraldehyde, N-hydroxysuccinimide esters, for example esters with 4-azidosalicylic acid, homobifunctional imidoesters including disuccinimidyl esters such as 3,3'-dithiobis (succinimidyl-propionate), and bifunctional maleimides such as bis-N-maleimido-1,8-octane. Derivatizing agents such as methyl-3-[(p-azido-phenyl) dithio] proptoimidate yield photoactivatable intermediates which are capable of forming cross-links in the presence of light. Alternatively, reactive water soluble matrices such as cyanogen bromide activated carbohydrates and the systems described in U.S. Pat. Nos. 3,959,080; 3,969,287; 3,691,016; 4,195,128; 4,247,642; 4,229,537; 4,055,635 and 4,330,440 are suitably modified for cross-linking the polymer and HSP. Covalent bonding to MSP amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, succinimidyl active esters, activated dithiocarbonate PEG, 2,4,5-trichlorophenylchloroformate or p-nitrophenylchloroformate activated PEG. Carboxyl groups are derivatized by coupling PEG-amine using carbodiimide.

Polymers are conjugated to the oligosaccharide substituents by chemical, e.g. metaperiodate, or enzymatic oxidation, e.g. glucose or galactose oxidase, (to produce the aldehyde derivative of the carbohydrate), followed by reaction with hydrazide or amino-derivatized polymers, in the same fashion as is described by Heitzmann et al., P.N.A.S., 71:3537–3541 (1974) or Bayer et al., Methods in Enzymology, 62:310 (1979), for the labeling of oligosaccharides with biotin or avidin. Further, other chemical or enzymatic methods which have been used heretofore to link oligosaccharides and polymers may be suitable. Substituted oligosaccharides are particularly advantageous since there are fewer carbohydrate substitutions than amino acid sites for derivatization, thus improving the stability, activity and homogeneity of the conjugate. Finally, the MSP oligosaccharide substituents are enzymatically modified to remove sugars, e.g. by neuraminidase digestion, as a final product or prior to polymer derivatization.

The polymer will bear a group which is directly reactive with an amino acid side chain, or the N- or C- terminus of MSP, or which is reactive with the multifunctional crosslinking agent. In general, polymers bearing such reactive groups are known for the preparation of immobilized proteins. In order to use such chemistries here, one should employ a water soluble polymer otherwise derivatized in the same fashion as insoluble polymers heretofore employed for protein immobilization. Cyanogen bromide activation is a particularly useful procedure to employ in crosslinking polysaccharides to MSP.

"Water soluble" in reference to the starting polymer means that the polymer or its reactive intermediate used for conjugation is sufficiently water soluble to participate in a derivatization reaction with MSP.

The degree of substitution of MSP will vary depending upon the number of reactive sites one he protein, whether intact or truncated MSP is used, whether the MSP is a fusion with a protein heterologous to MSP, the molecular weight, hydrophilicity and ocher characteristics of the polymer, and the particular sites chosen. In general, the MSP portion of the conjugate is substituted with about from 1 to 10 polymer molecules, while any heterologous sequence which is fused to MSP may be substituted with an essentially unlimited number of polymer molecules so long as the activity of the MSP moiety is not significantly adversely affected. The optimal degree of crosslinking is easily determined by an experimental matrix in which the time, temperature and other reaction conditions are varied to change the degree of substitution, after which the ability of the conjugates to bind matrix protein or ligand is determined.

The polymer, e.g., PEG is crosslinked to MSP by a wide variety of methods known per se for the covalent modification of proteins with nonproteinaceous polymers such as PEG. Certain of these methods, however, are not preferred for the purposes herein. Cyanuric chloride chemistry leads to many side reactions, including protein cross-linking. In addition, it may be particularly likely to lead co inactivation of proteins containing sulfhydryl groups. Carbonyl diimidazole chemistry (Beauchamp et al., "Anal. Biochem." 131:25–33 [1983]) requires high pH (>8.5), which can inactivate proteins. Moreover, since the "activated PEG" intermediate can react with water, a very large molar excess of "activated PEG" over protein is required. In general, aldehyde chemistry (Royer, U.S. Pat. No. 4,002,531) is preferred since it requires only a 40 fold molar excess of PEG and a 1–2 hr incubation. However, the manganese dioxide suggested by Royer for preparation of the PEG aldehyde is problematic "because of the pronounced tendency of PEG to form complexes with metal-based oxidizing agents" (Harris et al., "J. Polym. Sci., Polym. Chem. Ed." 22:341–352 [1984]). Use of a moffatt oxidation, utilizing DMSO and acetic anhydride, obviates this problem. In addition, the sodium borohydride suggested by Royer must be used at a high pH and has a significant tendency to reduce disulphide bonds. In contrast, sodium cyanoborohydride, which is effective at neutral pH, has very little tendency to reduce disulphide bonds.

The MSP conjugates of this invention typically are separated from unreacted starting materials by gel filtration. Most conveniently, MSP conjugates are eluted from hydrophobic interaction chromatography medium, e.g. alkyl Sepharose, by the use of a decreasing salt gradient. This, as well as the gel filtration approach described above, resolves conjugates on the basis of the degree of substitution.

The DNA encoding an MSP is obtained by known procedures, in most instances by reference to publications describing DNA encoding the MSP. In general, prokaryotes are used for cloning of MSP variant DNA sequences. For example, a λ-resistant strain of *E. coli* JM 101 for propagating M13 phase: Messing et al., Nucl. Acids. Res. 9(2) :309–321 [1981]); and *E. Coli* K12 strain 294 (ATCC No. 31446) are particularly useful. Other microbial strains which may be used include *E. Coli* B, or UM101. These examples are illustrative rather than limiting. Nucleic acid also is cloned using various well known in vitro amplification processes.

DNA encoding the variant MSPs are inserted for expression into vectors containing promoters and control sequences which are derived from species compatible with the intended host cell. The vector ordinarily, but need not, carry a replication site as well as one or more marker sequences with are capable of providing phenotypic selection in transformed cells. For example, *E. coil* is typically transformed using a derivative of pBR322 which is a plasmid derived from an *E. coli* species (Bolivar, et al., Gene 2: 95 [1977]). pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA constructions.

Promoters suitable for use with prokaryotic hosts illustratively include the β-lactamase and lactose promoter systems (Chang et al., Nature, 275:615 [1978]; and Goeddel et al., Nature 281:544 [1979]), alkaline phosphatase, the tryptophan (trp) promoter system (Goeddel, Nucleic Acids Res. 8: 4057 [1980]and EPO Appln. Publ. No. 36,776) and hybrid promoters such as the tac promoter (H. de Boer et al., Proc. Natl. Acad. Sci. USA 80: 21–25 [1983]). However, other functional bacterial promoters are suitable. Their nucleotide sequences are generally known, thereby enabling a skilled worker operably to ligate them to DNA encoding the MSP variant using linkers or adaptors to supply any required restriction sites (Siebenlist et al., Cell 20: 269 [1980]). Promoters for use in bacterial systems also will contain a Shine-Dalgarno (S.D.) sequence operably linked to the DNA encoding the anitgen.

In addition to prokaryotes, eukaryotic microbes such as yeast cultures also are useful as cloning or expression hosts. *Saccharomyces cerevisiase*, or common baker's yeast is the most commonly used eukaryotic microorganism, although a number of other strains are commonly available. For expression in Saccharomyces, the plasmid YRp7, for example, (Stinchcomb, et al., Nature 282:39 [1979]; Kingsman et al, Gene 7:141 [1979]; Tschemper et al., Gene 10:157 [1980]) is commonly used. This plasmid already contains the trp1 gene which provides a selection marker for a mutant strain of yeast lacking the ability to grow in tryptophan, for example ATCC no. 44076 or PEP4-1 (Jones, Genetics 85: 12 [1977]). The presence of the trp1 lesion as a characteristic of the yeast host cell genome then provides an effective means of selection by growth in the absence of tryptophan.

Suitable promoting sequences for use with yeast hosts include the promoters for 3-phosphoglycerate kinase (Hitzeman et al., J. Biol. Chem. 255:2073 [1980]) or other glycolytic enzymes (Hess et al., J. Adv. Enzyme Reg. 7: 149 [1968]; and Holland, Biochemistry 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., European Patent Publication No. 73,657A. Yeast enhancers also are advantageously used with yeast promoters.

Promoters for controlling transcription from vectors in mammalian host cells may be obtained from various sources, for example, the genomes of viruses such as polyoma, Simian Virus 40 (SV40), adenovirus, retroviruses, hepatitis-B virus and most preferably cytomegalovirus, or from heterologous mammalian promoters, e.g. the beta actin promoter. The early and late promoters of the SV40 virus are conveniently obtained as an SV40 restriction fragment which also contains the SV40 vital origin of replication. Fiers et at., Nature, 273: 113 (1978). The immediate early promoter of the human cytomegalovirus is conveniently obtained as a HindIII E restriction fragment. Greenaway, P. J. et al., Gene 18:355–360 (1982). Of course, promoters from the host cell or related species also are useful.

DNA transcription in higher eukaryotes is increased by inserting an enhancer sequence into the vector. Enhancers are cis-acting elements of DNA, usually from about 10 to 300 bp, that act to increase the transcription initiation capability of a promoter. Enhancers are relatively orientation and position independent having been found 5' (Laimins, L. et al., Proc. Natl. Acad. Sci. 78:993 [1981]) and 3' (Lusky, M. L., et al., Mol Cell Bio. 3: 1108 [1983]) to the transcription unit, within an intron (Banerji, J. L. et al., Cell 33: 729 [1983]) as well as within the coding sequence itself (Osborne, T. F., et al., Mol. Cell Bio. 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding the MSP.

Expression vector systems generally will contain a selection gene, also termed a selectable marker. Examples of suitable selectable markers for mammalian cells are dihydrofolate reductase (DHFR), thymidine kinass or neomycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented medium. Two examples are: CRO DRFR$^-$ cells and mouse LTK$^-$ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented medium. An alternative to supplementing the medium is to introduce an intact DHFR or TK gene into cells lacking the respective genes, thus altering their growth requirements. Individual cells which were not transformed with the DHFR or TK gene will not be capable of survival in non supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., J. Molec. Appl. Genet. 1: 327 (1982), mycophenolic acid, Mulligan, R. C. and Berg, P. Science 209: 1422 (1980) or hygromycin, Sugden, B. et al., Mol. Cell. Biol. 5: 410–413 (1985). The three examples given above employ bacterial genes under eukaryotic control to convey resistance to the appropriate drug G418 or neomycin (geneticin), xgpt (mycophenolic acid) or hygromycin, respectively.

"Amplification" refers to the increase or replication of an isolated region within a cell's chromosomal DNA. Amplification is achieved using a selection agent e.g. methotrexate (MTX) which is inactivated by DHFR. Amplification or the making of successive copies of the DHFR gene results in greater amounts of DHFR being produced in the face of greater amounts of MTX. Amplification pressure is applied notwithstanding the presence of endogenous DHFR, by adding ever greater amounts of MTX to the media. Amplification of a desired gene can be achieved by cotransfecting a mammalian host cell with a plasmid having a DNA encoding a desired protein and the DHFR or amplification gene permitting cointegration. One ensures that the cell requires more DHFR, which requirement is met by replication of the selection gene, by selecting only for cells that can grow in the presence of ever-greater MTX concentration. So long as the gene encoding a desired heterologous protein has cointegrated with the selection gene replication of this gene gives rise to replication of the gene encoding the desired protein. The result is that increased copies of the gene, i.e. an amplified gene, encoding the desired heterologous protein express more of the desired heterologous protein.

Preferred host cells for expressing the MSP variants of this invention are mammalian host-vector systems, examples of suitable hosts including: monkey kidney CV1 line transformed by SV40 (COS-7, ATCC CRL 1651); human embryonic kidney line (293, Graham, F. L. et al., J. Gen Virol. 36: 59 [1977] and 293S cells, either of which are equally satisfactory); baby hamster kidney cells (BHK, ATCC CCL 10); chinese hamster ovary-cells DHFR (CHO, Urlaub and Chasin, Proc. Natl. Acad. Sci. (USA) 77: 4216, [1980]); mouse sertoli cells (TM4, Mather, J. P., Biol. Reprod. 23: 243–251 [1980]); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51 cells); and TRI cells (Mather, J. P. et al., Annals N.Y. Acad. Sci. 383: 44–68 [1982]).

"Transformation" means introducing DNA into an organism so that the DNA is replicaple, either as an extrachromosomal element or by chromosomal integration. One suitable for transformation of the host cells is the method of Graham, F. and van der Eb, A., Virology 52: 456–457 (1973). However, other methods for introducing DNA into cells such as by nuclear injection or by protoplast fusion may also be used. If prokaryotic cells or cells which contain substantial cell walls are used as hosts, the preferred method of transfection is calcium treatment using calcium chloride as described by Cohen, F. N. es al., Proc. Natl. Acad. Sci. (USA), 69:2110 (1972).

Construction of suitable vectors containing the desired coding and control sequences employ standard and manipulative ligation techniques. Isolated plasmids or DNA fragments are cleaved, tailored, and religated in the form desired to form the plasmids required. Suitable procedures are well known for the construction described herein. See, for example, (Maniatis, T. et al., *Molecular Cloning*, 133–134 Cold Spring Harbor, [1982]; "Current Protocols in Molecular Biology", edited by Ausubel et al., [1987], pub. by Greene Publishing Associates & Wiley-interscience).

Ordinarily, DNA encoding each subunit of a given MSP (or transmembrane modified variant) is simultaneously cotransfected into the host cell, although such transfections can be done sequentially. MSP variants in which one subunit is exchanged for the analogous subunit of another MSP (to produce heterologous heterodimers) are produced by cotransforming a recombinant host (typically mamalian cell) with each of the heterologous subunits, for example, exchanging the fibronectin $\alpha$ subunit for the $\alpha$ subunit of GPIIb-IIIa (an $\alpha$ subunit exchange), or the fibronectin $\beta$ subunit for the $\beta$ subunit of GPIIb-IIIa ($\alpha$ $\beta$ subunit exchange).

Correct plasmid sequences are confirmed by transforming *E. coli* K12 strain 294 (ATCC 31446) with ligation mixtures, successful transformants selected by ampicillin or tetracycline resistance where appropriate, plasmids from the transformants prepared, and then analyzed by restriction enzyme digestion and/or sequenced by the method of Messing et al., Nucleic Acids Res. 9: 309 (1981) or by the method of Maxam et al., Methods in Enzymology 65: 499 (1980).

Host cells are transformed with the expression vectors of this invention. Thereafter they are cultured in appropriate culture media, e.g. containing substances for inducing promoters, selecting transformants or amplifying genes. The culture conditions, such as temperature, pH and the like, are those previously used with the host cell selected for expression, and will be apparent to the ordinarily skilled artisan. For expression of GPIIb-IIIa it is preferable that the culture medium contain calcium and magnesium salts since divalent cations are needed to enhance the stability of secreted GPIIb-IIIa and other calcium dependent MSPs.

The secreted MSP varianns are recovered and purified from the culture supernatants or lysates of recombinant hosts. Typically, the supernatants are concentrated by ultrafiltration, contacted with a ligand (e.g. RGD) or matrix protein affinity or immunoaffinity resin so as to adsorb the MSP variant, and eluted from the adsorbent. Optionally, the MSP is purified by HPLC, lectin columns, gel exclusion, hydrophobic interaction or ion exchange chromatography.

The purified MSP is formulated into conventional pharmacologically acceptable excipients.

The soluble MSP variants of this invention are useful in therapeutics, diagnostics and preparative procedures. In diagnostics, the soluble MSFs are employed in place of membrane extracts as standards or controls, or are labelled with a radioisotope or other detectable group for use in competitive-type radioimmuno- or radioreceptor assays for the MSP or its antibodies.

The soluble MSPs are crosslinked to insoluble supports by the methods described herein and employed for the purification of their ligands or matrix proteins, e.g. fibronectin, fibrinogen and the like. Alternatively, the soluble MSPs are used to adsorb ligand or matrix protein in solution, followed by precipitation by antisera, ammonium sulfate or the like in order to recover the ligand or matrix protein complex. The complex is then dissociated by HPLC, electrophoresis, gel chromatography or other conventional methods.

Therapeutic uses of soluble MSPs will be a function of the biological activity of each MSP, and will be apparent therefrom. The soluble MSP variants herein may act as agonists or antagonists of the corresponding native, membrane-bound receptors. The soluble GPIIB-IIIa receptor, for example, is useful as an anticoagulant and for the treatment of disorders associated with platelet aggregation, particularly in the prevention of reocclusion following thrombolytic therapy. Soluble matrix receptors, especially soluble GPIIb-IIIa, also are useful as antagonists to matrix-adhesion dependent neoplastic metastasis. Soluble LFA-1 variants are an antagonist of T-lymphocyte function, thereby being efficacious as immunosuppressive or anti-inflammatory agents, particularly in reperfusion injury. Soluble Mac-1 variants may find use in the treatment of complement activation disorders.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide or agarose gel to isolate the desired fragment.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally (Lawn, R. et al., Nucleitc Acids Res. 9: 6103–6114 [1981], and Goeddel, D. et al., Nucleitc Acids Res. 8: 4057 [1980]).

"Ligation" refers to the process of forming phosphodiester bonds between two double stranded nucleic acid fragments (Maniatis, T. et al., Id. at 146). Unless otherwise provided, ligation may be accomplished using known buffers and conditions with 10 units of T4 DNA ligase ("ligase") per 0.5 µg of approximately equimolar amounts of the DNA fragments to be ligated.

The following examples merely illustrate the best mode now contemplated for practicing the invention, but should not be construed to limit the invention. All literature citations herein are expressly incorporated by reference.

EXAMPLE 1

Cloning of Glycoprotein IIb (GPIIb) cDNA

Messenger RNA was prepared from cultured human erythroleukemia cells (HEL, ATCC TIB 180). An oligo(dT)-primed cDNA library was prepared using this mRNA in the bacteriophage lambda ZAP (Stratagene Cloning Systems). The lambda ZAP library was screened with a 45-mer oligonucleotide (261) derived from the 5' end of the published cDNA sequence for GPIIb from HEL cells (Poncz et al., "J. Biol. Chem." 262(18):8476–8482 [1987]). Several positively-hybridizing phage were purified, and the cDNA inserts they contained were subjected to restriction enzyme digestion analysis. From these results a phage which appeared to contain a full-length coding insert for GPIIb was selected for further analysis. DNA sequencing of this phage insert DNA gave over 300 bases which corresponded exactly with the published cDNA sequence from the 5' end of the mRNA (Poncz et al.) except having 4 additional bases on its 5' end. The cDNA insert was digested with EcoRI (this site being derived from the linkers ligated to the ends of the cDNAs during production of the library) and HindIII, which cuts the GPIIb insert uniquely downstream of the end of the coding sequence. This EcoRI to HindIII restriction fragment, containing the entire coding region for GPIIb was ligated into mammalian cell expression vector pRK5 (U.S. Ser. No. 7/097,472) which had been digested with EcoRI and HindIII, and expression vector GPIIb-pRK5 was recovered.

Construction of Full-Length Glycoprotein IIIa (GPIIIa) cDNA

A cDNA clone for GPIIIa, incomplete at its 5' end, was obtained (Rosa et al., "Blood" 72(2):593 [1988]). The cDNA was provided as an EcoRI (site derived from the cDNA library construction linker) to PstI (site downstream of the end of the coding sequence) insert in the plasmid vector pIBI20 (International Biotechnologies, Inc.) This plasmid was digested with HindIII to cut the plasmid at the unique HindIII site in pIBI20 downstream of the terminal PscI site in the cDNA insert, and incompletely with ApaI, to give a cDNA fragment bounded by the ApaI site at the 5' end of the sequence and HindIII from the plasmid vector. The relevant domain for the construction is shown below.

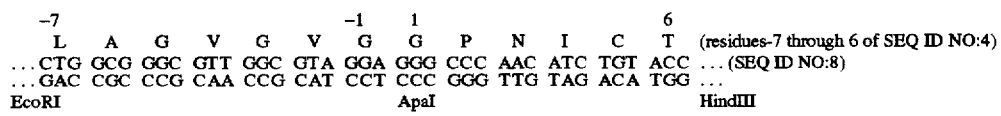

Synthetic complementary oligonucleotides were used to reconstruct a full-length coding construct for GPIIIa based on the published cloned cDNA sequence (Fitzgerald et al., "J. Biol Chem." 262(9):3936 [1987]). The oligonucleotide sequence, ending in ApaI, was ligated to the ApaI site of the above ARaI-HindIII fragment, to give a DNA fragment now bounded by EcoRI and HindIII. This EcoRI to HindIII fragment, containing the entire coding region for GPIIIa was ligated into pRK5 which had been digested with EcoRI and HindIII, and expression vector GPIIIa-pRK5 was recovered. The relevant oligonucleotide sequences are shown below.

```
                            -26
                                M   R   A   P   R   P   R   P   L   W
AAT TCT AGA GCC GCC ATG AGA GCA CGT CCT CGA CCA CGT CCT CTC TGG -
    GA TCT CGG CGG TAC TCT CGT GCA GGA GCT GGT GCA GGA GAG ACC -
EcoRI
    XbaI
```

```
                                                          -1   1
 A   T   V   L   A   L   G   A   L   A   G   V   G   V   G   P   (residues -26 through 2 of SEQ ID NO:4)
GCG ACT GTG CTG GCA CTG GGA GCA CTG GCT GGT GTT GGA GTA GGA GGG CC  (SEQ ID NO:9)
CGC TGA CAC GAC CGT GAC CCT CGT GAC CGA CCA CAA CCT CAT CCT C       (SEQ ID NO:10)
                                                            ApaI
```

The synthetic oligonucleotides were designed such that the amino acids encoded were identical to those predicted from the published cloned cDNAs (Fitzgerald et al., Rosa et al.), but the codons were not always identical with the naturally-occurring cloned cDNA. FIG. 3 compares the coding strands of the synthetic and natural sequences. Asterisks between each sequence indicate which nucleotides are identical. These changes were introduced for three reasons.

1. In light of difficulties encountered in sequencing the cDNA, we concluded that the cDNA could contain secondary structure adverse to translational efficiency. To minimize possible secondary structure in the mRNA produced from expression constructs, the percentage of G and C bases in the natural coding sequence was lessened by changing some codons to others which had a lower G and/or C content, but which coded for the same amino acid. These altered codons were chosen such that only codons used frequently in the remainder of the cDNA were substituted. Karnick et al., "J. Biol. Chem. 262(5):9255 (1987); Devlin et al., "Gene" 65:13 (1988).

2. The codon for arginine (R, amino acid −25), immediately following the initiator methionine codon (M −26), was changed from CGA to AGA. Kozak, "Nucl. Acids Res." 15(20):8125 [1987] and Kozak, "J. Mol. Biol." 196:947 [1987].

3. The DNA sequence upstream of the initiator methionine codon was not based on the natural DNA sequence. The synthetic complementary oligonucleotides were such that an EcoRI site was present at one end, followed by an XbaI recognition sequence, and then followed by a GCC GCC motif immediately upstream of the initiator methionine. Kozak, "J. Biol." Id.

The plasmids encoding GPIIb and GPIIIa (GPIIb-pRK5 and GPIIIa-pRK5) were transfected in 293S cells and cultured under conventional conditions for transient expression as described below. The cells were harvested and analyzed for GPIIb-IIIa expression. Expression was confined by the presence of correctly sized bands on a Western gel, immunologically visualized by FACS sorting, and immunoprecipitation of intact cells labeled metabolically with $S^{35}$ or by $^{125}I$ surface-labelling.

EXAMPLE 2

Construction of cDNA Encoding Truncated. GPIIb

The starting point for the construction of the GPIIb truncated form was the full-length coding construction for GPIIb described in Example 1. The relevant domain for this construction is shown below.

```
                                              putative
                                              transmembrane
                                              region
                          962
         L   R   A   L   E   E   R   A   I
   ...CTC CGG GCC TTG GAG GAG AGG GCC ATT ...
                                              (SEQ ID NO:11)
   ...GAG GCC CGG AAC CTC CTC TCC CGG TAA ...
   EcoRI        StyI                          (SEQ ID NO:12)
```

The DNA fragment from the EcoRI site (upstream of the initiator ATG codon) to the StyI site indicated above was isolated and ligated to complementary synthetic oligonucleotides such that the DNA sequence thus obtained coded for the natural GPIIb sequence up to amino acid residue 962 (arginine) and was then followed by a TGA stop codon.

```
                                    (residues 958 through 962 of
    A   L   E   E   R   Stop        (SEQ ID NO:2)
    C TTG GAG GAG AGG TGA TGA A     (SEQ ID NO:13)
        CTC CTC TCC ACT ACT TTC GA  (SEQ ID NO:14)
    StyI                HindIII
```

In the natural sequence, arginine 962 is followed by an approximately 26 amino acid putative hydrophobic transmembrane domain and a cytoplasmic domain (Poncz et al.). Thus, in this construction both of these domains have been deleted from the coding region of the construction. The end of the synthetic fragment terminated in a HindIII restriction site. The entire DNA fragment bounded by EcoRI and HindIII restriction sites was ligated into pRK5 which had been digested with EcoRI and HindIII. Expression vector GPIIbtrunc-pRK5 was recovered.

The EcoRI to HindIII fragment outlined above was rescued from GPIIbtrunc-pRK5 and subjected to analysis by DNA sequencing. Over 250 bases from each end of the insert were sequenced and corresponded exactly to that which was predicted.

Construction of cDNA Encoding Truncated GPIIIa

The starting point for the construction of the GPIIIa truncated form was the full-length coding construction for GPIIIa described in Example 1. The relevant domain for this construction is shown below.

```
                            putative transmembrane region
                      692
          P   K   G   P   D   I   L   L
   ...CCC AAG GGC CCT GAC ATC CTG GTG ...
                                              (SEQ ID NO:15)
   ...GGG TTC CCG GGA CTG TAG GAC CAC ...
   XbaI        ApaI                           (SEQ ID NO:16)
```

The DNA fragment from the XbaI site (upstream of the initiator ATG codon) to the ApaI site indicated below was isolated and ligated to complementary synthetic oligonucleotides such that the DNA sequence thus obtained coded for the natural GPIIIa sequence up to amino acid residue 692 (aspaitic acid) and was then followed by a TGA stop codon.

```
       G   P   D   Stop
          CT GAC TGA TGA GAT CTA         (SEQ ID NO:17)
          CCG GGA CTG ACT ACT CTA GAT TCG A   (SEQ ID NO:18)
          ApaI                            HindIII
```

In the natural sequence, aspartic acid 692 is followed by an approximately 29 amino acid putative hydrophobic transmembrane domain and a cytoplasmic domain (Fitzgerald et al.) Thus, in this construction both of these domains have been deleted from the coding region of the construction. The end of the synthetic fragment terminated in a HindIII restriction site. The entire fragment bounded by XbaI and HindIII restriction sites, was ligated into pRK5 previously digested with XbaI and HindIII and trunc expression vector GPIIIatrunc-pRK5 was recovered.

The XbaI to HindIII fragment outlined above was rescued from GPIIIatrunc-pRK5, and subjected to analysis by DNA sequencing. Over 200 bases from each end of the insert were sequenced and corresponded exactly to that which was predicted.

Expression of Truncated Human GPIIb-IIIa. Receptor in a Eukaryotic Host

Human embryonic kidney cells (293S) were cotransfected with the expression vectors GPIIbtrunc-pRK5 and GPIIIatrunc-pRK5 using $CaPO_4$ (Graham et al., "Virology" 52:456 [1973]) using the host system described in EP 260,148.

Transient Expression

High levels of transient expression were obtained when 293S cells were cotransfected with GPIIbtrunc-pRK5, GPIIIatrunc-pRK5 and adenovirus VA RNA-DNA (U.S. Ser. No. 07/101,712, Akusjarvietal, "Mol. Cell. Biol" 7:549 [1987]) and grown in standard growth media (50% Dulbeccos Modified Eagle Media, 50% F12 mixture, 2 nM L-glutamine and 10% fetal bovine serum). 16 hours after glycerol shock cells were transferred to serum free media (Dulbeccos Modified Eagle Media, 0.1% glucose, 10 µg/ml insulin) and grown for a further 48 hours, at which time cells and culture media were harvested. Conditioned cell culture fluid was centrifuged to remove contaminating cell debris and then quick frozen in dry ice-ethanol and stored at −70' C. until analyzed. Cells were removed from 6 cm plates by suspension in 0.6 ml of 150 nM NaCl, 10 Tris (pH 7.5), 1% Triton X-100, 2 mM PMSF, 0.5 µg/ml leupeptin and 2 µg/ml pepstatin A followed by extraction for 30 minutes on ice with vortexing. Cellular debris was removed by centrifugation at 10,000 g and samples stored at −70° C. The soluble GPIIb-IIIa was recovered by Q-Sepharose (fast-flow) chromatography with 10 column volumes of 20 nM MES buffer/1 mM $CaCl_{12}$ pH 6.5 and gradient eldlion over 0–400 mM Natl. The peak soluble GPIIb-IIIa tended to elute at about 200–250 mM NaCl. The eluate was concentrated to 3% of the column volume of an S-300 column, after which the concentrate was exclusion chromatographed on the a-350 column using 10 ma Tris/150 mM NaCl/1 $CaCl_2$ pH 7.5. Some of the full length GPIIb transfected into 293S cells associated with endogenous $\alpha_v$. The secretion of soluble GPIIb with soluble GPIIIa avoided the need to purify BPIIb-IIIa from the $\alpha_v\beta_3$ vitronectin receptor, as would have been the case if the full length subunits had been used. See Bodary et al., J. Biol. Chem. 32:18859 (Nov. 15, 1989).

Stable Expression

Stable 293S clones expressing truncated GPIIb-IIIa were established by co-transfection of GPIIbtrunc-pRK5 and GPIIIatrunc-pRK5 with pRSVneo (Gorman et al., "Science" 221:551–552 [1983]). Forty eight hours after transfection cells were passaged into standard growth media containing 800 µg/ml of G418. Two weeks later, G418 resistant clones were picked and grown in standard growth media containing 400 µg/ml of G418. Clones were grown for 48 hours in serum free medium and the conditioned culture medium assayed for the expression of secreted forms of GPIIb-IIIa by Westernblot analysis.

Analysis of Expressed Truncated GPIIb-IIIa

Transiently transfected cells were assayed for expression by pulse-chase analysis followed by immunoprecipitation using a panel of monoclonal antibodies generated against purified platelet GPIIb-IIIa. $S^{35}$-cysteine and -methionine metabolically labeled proteins were recovered from the culture fluid of cells cotransfected with both GPIIbtrunc-pRK5 and GPIIIatrunc-pRK5 as described above. Truncated GPIIb-IIIa was immunoprectpitated from cell culture fluid with a panel of mouse monoclonal antibodies (AP2 [Montgomery et al., "J. Clin. Invest." 71:385 (1983)], 2D2, 3A8, 4B12, and AP3 [Newman et al., "Blood" 65:227 (1985)]) by incubation with Protein A Sepharose CL4B (Pharmacia), bound to rabbit IgG antibodies directed against mouse IgG. Electrophoresis of the immunoprecipitated proteins demonstrated the secretion of recombinant truncated GPIIb-IIIa whose size was in agreement with the molecular weights expected of the modified cDNAs. Monoclonal antibodies specific to the GPIIb-IIIa complex (AP2), GPIIb (2D2, 3A8) and GPIIIa (4B12, AP3) all immunoprecipitate both the GPIIb and GPIIIa truncated proteins, demonstrating that the recombinant secreted proteins are present in the form of a complex. Cells which received no DNA or the GPIIbtrunc-pRK5 alone or GPIIIatrunc-pRK5 alone do not secrete proteins at levels which are detectable by monoclonal antibodies to GPIIb or GPIIIa.

The expression of individual subunits of GPIIb or GPIIIa in transiently transfected cells was demonstrated using Western blot analysis. Cells were extracted as described above and culture media (recovered as above) were concentrated 2-fold by ultrafiltration and analyzed by electrophoresis on polyacrylamide gels (Laemmli, U. K., "Nature" 227:680–685 [1970]) and by Western Blotting (Towbin et al., Proc. Natl. Acad. Sci. USA 76:4350–4354 [1979]). Mouse monoclonal antibodies specific for GPIIb and GPIIIa were used in this analysis. Horse radish peroxidas-conjugated antibodies directed against the murine monoclonals were used to visualize the individual GPIIbtrunc and GPIIIatrunc proteins in the extracts.

The stable clones expressing the GPIIb-IIIa truncated constructs were shown to secrete the recombinant proteins of the expected sizes using Western blot analysis.

That the GPIIb-IIIa trunc proteins secreted from stable clones were present as a complex was demonstrated by their detection, after direct transfer of culture medium to nitrocellulose by aspiration, with monoclonal antibody AP2.

The truncated GPIIb or GPIIIa proteins were not detected in culture media when expressed as individual subunits: either they are not secreted or the efficiency of secretion is reduced to levels which preclude detection by immunoprecipitation or by Western blot analysis.

EXAMPLE 3

Demonstration of Fibrinogen Binding of Secreted Human GPIIb-IIIa Polypeptide Complex The functional activity of the secreted truncated GPIIb-IIIa is shown by its specific absorption to an affinity matrix containing the natural ligand, fibrinogen, for the GPIIb-IIIa receptor.

A stable clone from Example 2 which was expressing the GPIIb-IIIa truncated polypeptide complex was grown for 20 hours under serum free conditions (DMEM culture medium, 0.1% glucose, 10 µg/ml insulin, 1.5 µg/ml L-cysteine, 2.4 µg/ml L-methionine, 200 µCi/ml $S^{35}$ methionine and 200 µCi/ml $S^{35}$ cystsine). The conditioned cell culture fluid was first concentrated by ultrafiltration then purified by fibrinogen affinity chromatography. The fibrinogen affinity column was produced by coupling highly purified human fibrinogen to CNBr-activated Sepharose 4B (Pharmacia) using the manufacturer's recommended procedure. The concentrated cell culture fluid was applied first to a control Tris/ethanolamine reacted CNBr-activated Sepharose 4B column and the unbound material applied directly to the fibrinogen-Sepharose column. The contaminating proteins were washed away at room temperature with phosphate buffered saline solution containing 1 mM $Ca^{2+}$, 1 mM $Mg^{2+}$, 25 mM octylglucoside (OG) and 2 mM phenylmethylsulfonylfluoride (PMSF). The bound GPIIb-IIIa was eluted from the column at room temperature with phosphate buffered saline containing 15 mMg DTA, 25 mM OG and 2mM PMSF. The eluted GPIIb-IIIa was then concentrated by ultrafiltration and the subunits of expected molecular weight identified by autoradiography and by Western blot analysis using monoclonal antibodies specific to GPIIb (3A8) and GPIIIa (4B12). The specificity of the binding to the fibrinogen column is shown by the absence of the protein in the eluate from the control column determined by both methods.

EXAMPLE 4

Expression of LFA-1 and Mac-1 truncations

LFA-1 and Mac-1 are integrins having identical beta chains (beta-2) and distinct alpha chains (alpha L and alpha M, respectively). In this study the full length chains were transformed into host cells. In addition, the DNA encoding the transmembrane domains of the alpha and beta chains of each of these integrins was deleted and the truncated DNAs transformed into host cells for coexpression.

Transformants with full length LFA-1 alphaL chain did not express any detectable cell bound alphaL, but cotranformation with truncated alphaL and truncated beta-2, or with truncated alphaM and truncated beta-2, resulted in the secretion of the truncated heterodimers. Interestingly, transformation with the full length alphaM chain of Mac-1 alone did yield cell surface alphaM. It has not been confirmed that this product represents a stable alphaM monomer since it is conceivable that the recombinant alphaM chain became associated with a beta chain endogenous to the host cell.

We claim:

1. A host cell transformed with DNA encoding a soluble analogue of a multiple subunit polypeptide (MSP), wherein the MSP is an integrin comprising an $\alpha$ and a $\beta$ subunit, said integrin selected from the group consisting of GPIIb-IIIa; p-150, 95, Mac-1, LFA-1, a leukocyte adhesion receptor; a member of the VLA family; and a heterodimeric receptor that participates directly in intercellular adhesion or adhesion of cells to extracellular matrix proteins;

wherein the soluble analogue comprises (1) a first MSP subunit variant fused at its C-terminus to an immunoglobulin constant domain and (2) a second MSP subunit variant which is not fused to an immunoglobulin constant domain, wherein the first and the second MSP subunit variants associate naturally with each other, are encoded by discrete nucleic acids, and lack a functional membrane anchor domain.

2. A method comprising culturing the host cell of claim 1 and recovering the soluble analogue from the host cell culture.

3. The host cell of claim 1 wherein the membrane anchor domains of the $\alpha$- and $\beta$-subunits of the integrin are deleted.

4. The host cell of claim 3 wherein the cytoplasmic domains of the $\alpha$- and $\beta$-subunits of the integrin are deleted.

5. The host cell of claim 1 further comprising DNA encoding an unfused immunoglobulin chain.

6. The host cell of claim 5 wherein the unfused immunoglobulin chain comprises a variable domain.

7. The host cell of claim 5 wherein the unfused immunoglobulin chain is a light chain with its variable domain deleted and the immunoglobulin constant domain fused to the first MSP subunit variant is a heavy chain constant domain.

8. The host cell of claim 1 further comprising DNA encoding a heavy unfused immunoglobulin chain and a light unfused immunoglobulin chain each of which contain a variable domain, wherein the variable domains bind to an antigen.

9. A method comprising culturing the host cell of claim 8 and recovering the soluble analogue from the host cell culture.

10. The host cell of claim 1 wherein the transmembrane domain of the first MSP chain is deleted.

11. The host cell of claim 1 wherein the transmembrane domain of the second MSP chain is deleted.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 3017 base pairs
        ( B ) TYPE: Nucleic Acid
        ( C ) STRANDEDNESS: Double
        ( D ) TOPOLOGY: Linear ( x i ) SEQUENCE DESCRIPTION: SEQ ID NO:1:

```
GAATTCTCGA  GCTCGTCGAC  CGGAAG     ATG  GCC  AGA  GCT  TTG   41
                                   Met  Ala  Arg  Ala  Leu
                                   -31  -30

TGT  CCA  CTG  CAA  GCC  CTC  TGG  CTT  CTG  GAG  TGG  GTG  CTG   80
Cys  Pro  Leu  Gln  Ala  Leu  Trp  Leu  Leu  Glu  Trp  Val  Leu
     -25                      -20                      -15

CTG  CTC  TTG  GGA  CCT  TGT  GCT  GCC  CCT  CCA  GCC  TGG  GCC   119
Leu  Leu  Leu  Gly  Pro  Cys  Ala  Ala  Pro  Pro  Ala  Trp  Ala
               -10                      -5

TTG  AAC  CTG  GAC  CCA  GTG  CAG  CTC  ACC  TTC  TAT  GCA  GGC   158
Leu  Asn  Leu  Asp  Pro  Val  Gln  Leu  Thr  Phe  Tyr  Ala  Gly
 1             5                        10

CCC  AAT  GGC  AGC  CAG  TTT  GGA  TTT  TCA  CTG  GAC  TTC  CAC   197
Pro  Asn  Gly  Ser  Gln  Phe  Gly  Phe  Ser  Leu  Asp  Phe  His
     15                  20                              25

AAG  GAC  AGC  CAT  GGG  AGA  GTG  GCC  ATC  GTG  GTG  GGC  GCC   236
Lys  Asp  Ser  His  Gly  Arg  Val  Ala  Ile  Val  Val  Gly  Ala
                30                        35

CCG  CGG  ACC  CTG  GGC  CCC  AGC  CAG  GAG  GAG  ACG  GGC  GGC   275
Pro  Arg  Thr  Leu  Gly  Pro  Ser  Gln  Glu  Glu  Thr  Gly  Gly
40                       45                        50

GTG  TTC  CTG  TGC  CCC  TGG  AGG  GCC  GAG  GGC  GGC  CAG  TGC   314
Val  Phe  Leu  Cys  Pro  Trp  Arg  Ala  Glu  Gly  Gly  Gln  Cys
```

|     |     |     |     |     |     |     |     |     |     |     |     |     |
|-----|-----|-----|-----|-----|-----|-----|-----|-----|-----|-----|-----|-----|
|     | 55  |     |     |     |     | 60  |     |     |     |     | 65  |     |
| CCC | TCG | CTG | CTC | TTT | GAC | CTC | CGT | GAT | GAG | ACC | CGA | AAT | 353
| Pro | Ser | Leu | Leu | Phe | Asp | Leu | Arg | Asp | Glu | Thr | Arg | Asn |
|     |     |     |     | 70  |     |     |     |     | 75  |     |     |     |
| GTA | GGC | TCC | CAA | ACT | TTA | CAA | ACC | TTC | AAG | GCC | CGC | CAA | 392
| Val | Gly | Ser | Gln | Thr | Leu | Gln | Thr | Phe | Lys | Ala | Arg | Gln |
|     | 80  |     |     |     |     | 85  |     |     |     |     | 90  |     |
| GGA | CTG | GGG | GCG | TCG | GTC | GTC | AGC | TGG | AGC | GAC | GTC | ATT | 431
| Gly | Leu | Gly | Ala | Ser | Val | Val | Ser | Trp | Ser | Asp | Val | Ile |
|     |     |     |     | 95  |     |     |     |     | 100 |     |     |     |
| GTG | GCC | TGC | GCC | CCC | TGG | CAG | CAC | TGG | AAC | GTC | CTA | GAA | 470
| Val | Ala | Cys | Ala | Pro | Trp | Gln | His | Trp | Asn | Val | Leu | Glu |
| 105 |     |     |     |     | 110 |     |     |     |     | 115 |     |     |
| AAG | ACT | GAG | GAG | GCT | GAG | AAG | ACG | CCC | GTA | GGT | AGC | TGC | 509
| Lys | Thr | Glu | Glu | Ala | Glu | Lys | Thr | Pro | Val | Gly | Ser | Cys |
|     |     | 120 |     |     |     |     | 125 |     |     |     |     | 130 |
| TTT | TTG | GCT | CAG | CCA | GAG | AGC | GGC | CGC | CGC | GCC | GAG | TAC | 548
| Phe | Leu | Ala | Gln | Pro | Glu | Ser | Gly | Arg | Arg | Ala | Glu | Tyr |
|     |     |     |     | 135 |     |     |     |     | 140 |     |     |     |
| TCC | CCC | TGT | CGC | GGG | AAC | ACC | CTG | AGC | CGC | ATT | TAC | GTG | 587
| Ser | Pro | Cys | Arg | Gly | Asn | Thr | Leu | Ser | Arg | Ile | Tyr | Val |
|     | 145 |     |     |     |     | 150 |     |     |     |     | 155 |     |
| GAA | AAT | GAT | TTT | AGC | TGG | GAC | AAG | CGT | TAC | TGT | GAA | GCG | 626
| Glu | Asn | Asp | Phe | Ser | Trp | Asp | Lys | Arg | Tyr | Cys | Glu | Ala |
|     |     |     | 160 |     |     |     |     | 165 |     |     |     |     |
| GGC | TTC | AGC | TCC | GTG | GTC | ACT | CAG | GCC | GGA | GAG | CTG | GTG | 665
| Gly | Phe | Ser | Ser | Val | Val | Thr | Gln | Ala | Gly | Glu | Leu | Val |
| 170 |     |     |     |     | 175 |     |     |     |     | 180 |     |     |
| CTT | GGG | GCT | CCT | GGC | GGC | TAT | TAT | TTC | TTA | GGT | CTC | CTG | 704
| Leu | Gly | Ala | Pro | Gly | Gly | Tyr | Tyr | Phe | Leu | Gly | Leu | Leu |
|     |     |     |     | 185 |     |     |     |     | 190 |     |     | 195 |
| GCC | CAG | GCT | CCA | GTT | GCG | GAT | ATT | TTC | TCG | AGT | TAC | CGC | 743
| Ala | Gln | Ala | Pro | Val | Ala | Asp | Ile | Phe | Ser | Ser | Tyr | Arg |
|     |     |     |     | 200 |     |     |     |     | 205 |     |     |     |
| CCA | GGC | ATC | CTT | TTG | TGG | CAC | GTG | TCC | TCC | CAG | AGC | CTC | 782
| Pro | Gly | Ile | Leu | Leu | Trp | His | Val | Ser | Ser | Gln | Ser | Leu |
|     | 210 |     |     |     |     | 215 |     |     |     |     | 220 |     |
| TCC | TTT | GAC | TCC | AGC | AAC | CCA | GAG | TAC | TTC | GAC | GGC | TAC | 821
| Ser | Phe | Asp | Ser | Ser | Asn | Pro | Glu | Tyr | Phe | Asp | Gly | Tyr |
|     |     |     | 225 |     |     |     |     | 230 |     |     |     |     |
| TGG | GGG | TAC | TCG | GTG | GCC | GTG | GGC | GAG | TTC | GAC | GGG | GAT | 860
| Trp | Gly | Tyr | Ser | Val | Ala | Val | Gly | Glu | Phe | Asp | Gly | Asp |
| 235 |     |     |     |     | 240 |     |     |     |     | 245 |     |     |
| CTC | AAC | ACT | ACA | GAA | TAT | GTC | GTC | GGT | GCC | CCC | ACT | TGG | 899
| Leu | Asn | Thr | Thr | Glu | Tyr | Val | Val | Gly | Ala | Pro | Thr | Trp |
|     |     |     | 250 |     |     |     |     | 255 |     |     |     | 260 |
| AGC | TGG | ACC | CTG | GGA | GCG | GTG | GAA | ATT | TTG | GAT | TCC | TAC | 938
| Ser | Trp | Thr | Leu | Gly | Ala | Val | Glu | Ile | Leu | Asp | Ser | Tyr |
|     |     |     |     | 265 |     |     |     |     | 270 |     |     |     |
| TAC | CAG | AGG | CTG | CAT | CGG | CTG | CGC | GCA | GAG | CAG | ATG | GCG | 977
| Tyr | Gln | Arg | Leu | His | Arg | Leu | Arg | Ala | Glu | Gln | Met | Ala |
|     | 275 |     |     |     |     | 280 |     |     |     |     | 285 |     |
| TCG | TAT | TTT | GGG | CAT | TCA | GTG | GCT | GTC | ACT | GAC | GTC | AAC | 1016
| Ser | Tyr | Phe | Gly | His | Ser | Val | Ala | Val | Thr | Asp | Val | Asn |
|     |     |     | 290 |     |     |     |     | 295 |     |     |     |     |
| GGG | GAT | GGG | AGG | CAT | GAT | CTG | CTG | GTG | GGC | GCT | CCA | CTG | 1055
| Gly | Asp | Gly | Arg | His | Asp | Leu | Leu | Val | Gly | Ala | Pro | Leu |
| 300 |     |     |     |     | 305 |     |     |     |     | 310 |     |     |
| TAT | ATG | GAG | AGC | CGG | GCA | GAC | CGA | AAA | CTG | GCC | GAA | GTG | 1094
| Tyr | Met | Glu | Ser | Arg | Ala | Asp | Arg | Lys | Leu | Ala | Glu | Val |

```
                    315                      320                           325
GGG  CGT  GTG  TAT  TTG  TTC  CTG  CAG  CCG  CGA  GGC  CCC  CAC     1133
Gly  Arg  Val  Tyr  Leu  Phe  Leu  Gln  Pro  Arg  Gly  Pro  His
                    330                      335

GCG  CTG  GGT  GCC  CCC  AGC  CTC  CTG  CTG  ACT  GGC  ACA  CAG     1172
Ala  Leu  Gly  Ala  Pro  Ser  Leu  Leu  Leu  Thr  Gly  Thr  Gln
          340                      345                      350

CTC  TAT  GGG  CGA  TTC  GGC  TCT  GCC  ATC  GCA  CCC  CTG  GGC     1211
Leu  Tyr  Gly  Arg  Phe  Gly  Ser  Ala  Ile  Ala  Pro  Leu  Gly
                    355                      360

GAC  CTC  GAC  CGG  GAT  GGC  TAC  AAT  GAC  ATT  GCA  GTG  GCT     1250
Asp  Leu  Asp  Arg  Asp  Gly  Tyr  Asn  Asp  Ile  Ala  Val  Ala
365                      370                      375

GCC  CCC  TAC  GGG  GGT  CCC  AGT  GGC  CGG  GGC  CAA  GTG  CTG     1289
Ala  Pro  Tyr  Gly  Gly  Pro  Ser  Gly  Arg  Gly  Gln  Val  Leu
          380                      385                      390

GTG  TTC  CTG  GGT  CAG  AGT  GAG  GGG  CTG  AGG  TCA  CGT  CCC     1328
Val  Phe  Leu  Gly  Gln  Ser  Glu  Gly  Leu  Arg  Ser  Arg  Pro
                    395                      400

TCC  CAG  GTC  CTG  GAC  AGC  CCC  TTC  CCC  ACA  GGC  TCT  GCC     1367
Ser  Gln  Val  Leu  Asp  Ser  Pro  Phe  Pro  Thr  Gly  Ser  Ala
          405                      410                      415

TTT  GGC  TTC  TCC  CTT  CGA  GGT  GCC  GTA  GAC  ATC  GAT  GAC     1406
Phe  Gly  Phe  Ser  Leu  Arg  Gly  Ala  Val  Asp  Ile  Asp  Asp
                    420                      425

AAC  GGA  TAC  CCA  GAC  CTG  ATC  GTG  GGA  GCT  TAC  GGG  GCC     1445
Asn  Gly  Tyr  Pro  Asp  Leu  Ile  Val  Gly  Ala  Tyr  Gly  Ala
430                      435                      440

AAC  CAG  GTG  GCT  GTG  TAC  AGA  GCT  CAG  CCA  GTG  GTG  AAG     1484
Asn  Gln  Val  Ala  Val  Tyr  Arg  Ala  Gln  Pro  Val  Val  Lys
          445                      450                      455

GCC  TCT  GTC  CAG  CTA  CTG  GTG  CAA  GAT  TCA  CTG  AAT  CCT     1523
Ala  Ser  Val  Gln  Leu  Leu  Val  Gln  Asp  Ser  Leu  Asn  Pro
                    460                      465

GCT  GTG  AAG  AGC  TGT  GTC  CTA  CCT  CAG  ACC  AAG  ACA  CCC     1562
Ala  Val  Lys  Ser  Cys  Val  Leu  Pro  Gln  Thr  Lys  Thr  Pro
          470                      475                      480

GTG  AGC  TGC  TTC  AAC  ATC  CAG  ATG  TGT  GTT  GGA  GCC  ACT     1601
Val  Ser  Cys  Phe  Asn  Ile  Gln  Met  Cys  Val  Gly  Ala  Thr
                    485                      490

GGG  CAC  AAC  ATT  CCT  CAG  AAG  CTA  TCC  CTA  AAT  GCC  GAG     1640
Gly  His  Asn  Ile  Pro  Gln  Lys  Leu  Ser  Leu  Asn  Ala  Glu
495                      500                      505

CTG  CAG  CTG  GAC  CGG  CAG  AAG  CCC  CGC  CAG  GGC  CGG  CGG     1679
Leu  Gln  Leu  Asp  Arg  Gln  Lys  Pro  Arg  Gln  Gly  Arg  Arg
          510                      515                      520

GTG  CTG  CTG  CTG  GGC  TCT  CAA  CAG  GCA  GGC  ACC  ACC  CTG     1718
Val  Leu  Leu  Leu  Gly  Ser  Gln  Gln  Ala  Gly  Thr  Thr  Leu
                    525                      530

AAC  CTG  GAT  CTG  GGC  GGA  AAG  CAC  AGC  CCC  ATC  TGC  CAC     1757
Asn  Leu  Asp  Leu  Gly  Gly  Lys  His  Ser  Pro  Ile  Cys  His
535                      540                      545

ACC  ACC  ATG  GCC  TTC  CTT  CGA  GAT  GAG  GCA  GAC  TTC  CGG     1796
Thr  Thr  Met  Ala  Phe  Leu  Arg  Asp  Glu  Ala  Asp  Phe  Arg
          550                      555

GAC  AAG  CTG  AGC  CCC  ATT  GTG  CTC  AGC  CTC  AAT  GTG  TCC     1835
Asp  Lys  Leu  Ser  Pro  Ile  Val  Leu  Ser  Leu  Asn  Val  Ser
560                      565                      570

CTA  CCG  CCC  ACG  GAG  GCT  GGA  ATG  GCC  CCT  GCT  GTC  GTG     1874
Leu  Pro  Pro  Thr  Glu  Ala  Gly  Met  Ala  Pro  Ala  Val  Val
```

-continued

| | | 575 | | | | 580 | | | | 585 | | | |
|---|---|---|---|---|---|---|---|---|---|---|---|---|---|
| CTG | CAT | GGA | GAC | ACC | CAT | GTG | CAG | GAG | CAG | ACA | CGA | ATC | 1913 |
| Leu | His | Gly | Asp | Thr | His | Val | Gln | Glu | Gln | Thr | Arg | Ile | |
| | | | | 590 | | | | | 595 | | | | |
| GTC | CTG | GAC | TGT | GGG | GAA | GAT | GAC | GTA | TGT | GTG | CCC | CAG | 1952 |
| Val | Leu | Asp | Cys | Gly | Glu | Asp | Asp | Val | Cys | Val | Pro | Gln | |
| 600 | | | | | 605 | | | | | 610 | | | |
| CTT | CAG | CTC | ACT | GCC | AGC | GTG | ACG | GGC | TCC | CCG | CTC | CTA | 1991 |
| Leu | Gln | Leu | Thr | Ala | Ser | Val | Thr | Gly | Ser | Pro | Leu | Leu | |
| | | | 615 | | | | | 620 | | | | | |
| GTT | GGG | GCA | GAT | AAT | GTC | CTG | GAG | CTG | CAG | ATG | GAC | GCA | 2030 |
| Val | Gly | Ala | Asp | Asn | Val | Leu | Glu | Leu | Gln | Met | Asp | Ala | |
| 625 | | | | | 630 | | | | | 635 | | | |
| GCC | AAC | GAG | GGC | GAG | GGG | GCC | TAT | GAA | GCA | GAG | CTG | GCC | 2069 |
| Ala | Asn | Glu | Gly | Glu | Gly | Ala | Tyr | Glu | Ala | Glu | Leu | Ala | |
| | | | 640 | | | | | 645 | | | | | 650 |
| GTG | CAC | CTG | CCC | CAG | GGC | GCC | CAC | TAC | ATG | CGG | GCC | CTA | 2108 |
| Val | His | Leu | Pro | Gln | Gly | Ala | His | Tyr | Met | Arg | Ala | Leu | |
| | | | | 655 | | | | | 660 | | | | |
| AGC | AAT | GTC | GAG | GGC | TTT | GAG | AGA | CTC | ATC | TGT | AAT | CAG | 2147 |
| Ser | Asn | Val | Glu | Gly | Phe | Glu | Arg | Leu | Ile | Cys | Asn | Gln | |
| 665 | | | | | 670 | | | | | 675 | | | |
| AAG | AAG | GAG | AAT | GAG | ACC | AGG | GTG | GTG | CTG | TGT | GAG | CTG | 2186 |
| Lys | Lys | Glu | Asn | Glu | Thr | Arg | Val | Val | Leu | Cys | Glu | Leu | |
| | | | 680 | | | | | 685 | | | | | |
| GGC | AAC | CCC | ATG | AAG | AAG | AAC | GCC | CAG | ATA | GGA | ATC | GCG | 2225 |
| Gly | Asn | Pro | Met | Lys | Lys | Asn | Ala | Gln | Ile | Gly | Ile | Ala | |
| 690 | | | | | 695 | | | | | 700 | | | |
| ATG | TTG | GTG | AGC | GTG | GGG | AAT | CTG | GAA | GAG | GCT | GGG | GAG | 2264 |
| Met | Leu | Val | Ser | Val | Gly | Asn | Leu | Glu | Glu | Ala | Gly | Glu | |
| | | | 705 | | | | | 710 | | | | | 715 |
| TCT | GTG | TCC | TTC | CAG | CTG | CAG | ATA | CGG | AGC | AAG | AAC | AGC | 2303 |
| Ser | Val | Ser | Phe | Gln | Leu | Gln | Ile | Arg | Ser | Lys | Asn | Ser | |
| | | | | 720 | | | | | 725 | | | | |
| CAG | AAT | CCA | AAC | AGC | AAG | ATT | GTG | CTG | CTG | GAC | GTG | CCG | 2342 |
| Gln | Asn | Pro | Asn | Ser | Lys | Ile | Val | Leu | Leu | Asp | Val | Pro | |
| | 730 | | | | | 735 | | | | | 740 | | |
| GTC | CGG | GCA | GAG | GCC | CAA | GTG | GAG | CTG | CGA | GGG | AAC | TCC | 2381 |
| Val | Arg | Ala | Glu | Ala | Gln | Val | Glu | Leu | Arg | Gly | Asn | Ser | |
| | | | 745 | | | | | 750 | | | | | |
| TTT | CCA | GCC | TCC | CTG | GTG | GTG | GCA | GCA | GAA | GAA | GGT | GAG | 2420 |
| Phe | Pro | Ala | Ser | Leu | Val | Val | Ala | Ala | Glu | Glu | Gly | Glu | |
| 755 | | | | | 760 | | | | | 765 | | | |
| AGG | GAG | CAG | AAC | AGC | TTG | GAC | AGC | TGG | GGA | CCC | AAA | GTG | 2459 |
| Arg | Glu | Gln | Asn | Ser | Leu | Asp | Ser | Trp | Gly | Pro | Lys | Val | |
| | | 770 | | | | | 775 | | | | | 780 | |
| GAG | CAC | ACC | TAT | GAG | CTC | CAC | AAC | AAT | GGC | CCT | GGG | ACT | 2498 |
| Glu | His | Thr | Tyr | Glu | Leu | His | Asn | Asn | Gly | Pro | Gly | Thr | |
| | | | | 785 | | | | | 790 | | | | |
| GTG | AAT | GGT | CTT | CAC | CTC | AGC | ATC | CAC | CTT | CCG | GGA | CAG | 2537 |
| Val | Asn | Gly | Leu | His | Leu | Ser | Ile | His | Leu | Pro | Gly | Gln | |
| | 795 | | | | | 800 | | | | | 805 | | |
| TCC | CAG | CCC | TCC | GAC | CTG | CTC | TAC | ATC | CTG | GAT | ATA | CAG | 2576 |
| Ser | Gln | Pro | Ser | Asp | Leu | Leu | Tyr | Ile | Leu | Asp | Ile | Gln | |
| | | | 810 | | | | | 815 | | | | | |
| CCC | CAG | GGG | GGC | CTT | CAG | TGC | TTC | CCA | CAG | CCT | CCT | GTC | 2615 |
| Pro | Gln | Gly | Gly | Leu | Gln | Cys | Phe | Pro | Gln | Pro | Pro | Val | |
| 820 | | | | | 825 | | | | | 830 | | | |
| AAC | CCT | CTC | AAG | GTG | GAC | TGG | GGG | CTG | CCC | ATC | CCC | AGC | 2654 |
| Asn | Pro | Leu | Lys | Val | Asp | Trp | Gly | Leu | Pro | Ile | Pro | Ser | |

|   |   |   |   |   | 835 |   |   |   |   | 840 |   |   |   |   | 845 |   |   |
|---|---|---|---|---|---|---|---|---|---|---|---|---|---|---|---|---|---|
| CCC | TCC | CCC | ATT | CAC | CCG | GCC | CAT | CAC | AAG | CGG | GAT | CGC | 2693 |
| Pro | Ser | Pro | Ile | His | Pro | Ala | His | His | Lys | Arg | Asp | Arg |   |
|   |   |   | 850 |   |   |   |   |   | 855 |   |   |   |   |

```
AGA CAG ATC TTC CTG CCA GAG CCC GAG CAG CCC TCG AGG   2732
Arg Gln Ile Phe Leu Pro Glu Pro Glu Gln Pro Ser Arg
    860             865             870

CTT CAG GAT CCA GTT CTC GTA AGC TGC GAC TCG GCG CCC   2771
Leu Gln Asp Pro Val Leu Val Ser Cys Asp Ser Ala Pro
            875             880

TGT ACT GTG GTG CAG TGT GAC CTG CAG GAG ATG GCG CGC   2810
Cys Thr Val Val Gln Cys Asp Leu Gln Glu Met Ala Arg
885             890             895

GGG CAG CGG GCC ATG GTC ACG GTG CTG GCC TTC CTG TGG   2849
Gly Gln Arg Ala Met Val Thr Val Leu Ala Phe Leu Trp
    900             905             910

CTG CCC AGC CTC TAC CAG AGG CCT CTG GAT CAG TTT GTG   2888
Leu Pro Ser Leu Tyr Gln Arg Pro Leu Asp Gln Phe Val
                915             920

CTG CAG TCG CAC GCA TGG TTC AAC GTG TCC TCC CTC CCC   2927
Leu Gln Ser His Ala Trp Phe Asn Val Ser Ser Leu Pro
    925             930             935

TAT GCG GTG CCC CCG CTC AGC CTG CCC CGA GGG GAA GCT   2966
Tyr Ala Val Pro Pro Leu Ser Leu Pro Arg Gly Glu Ala
            940             945

CAG GTG TGG ACA CAG CTG CTC CGG GCC TTG GAG GAG AGG   3005
Gln Val Trp Thr Gln Leu Leu Arg Ala Leu Glu Glu Arg
950             955             960     962

T GATG AAAGCTT   3017
```

( 2 ) INFORMATION FOR SEQ ID NO:2:

( i ) SEQUENCE CHARACTERISTICS:
        ( A ) LENGTH: 993 amino acids
        ( B ) TYPE: Amino Acid
        ( D ) TOPOLOGY: Linear ( x i ) SEQUENCE DESCRIPTION: SEQ ID NO:2:

```
Met Ala Arg Ala Leu Cys Pro Leu Gln Ala Leu Trp Leu Leu Glu
-31 -30             -25                 -20

Trp Val Leu Leu Leu Leu Gly Pro Cys Ala Ala Pro Pro Ala Trp
        -15             -10                 -5

Ala Leu Asn Leu Asp Pro Val Gln Leu Thr Phe Tyr Ala Gly Pro
        1               5               10

Asn Gly Ser Gln Phe Gly Phe Ser Leu Asp Phe His Lys Asp Ser
15              20              25

His Gly Arg Val Ala Ile Val Val Gly Ala Pro Arg Thr Leu Gly
30              35              40

Pro Ser Gln Glu Glu Thr Gly Gly Val Phe Leu Cys Pro Trp Arg
45              50              55

Ala Glu Gly Gly Gln Cys Pro Ser Leu Leu Phe Asp Leu Arg Asp
60              65              70

Glu Thr Arg Asn Val Gly Ser Gln Thr Leu Gln Thr Phe Lys Ala
75              80              85

Arg Gln Gly Leu Gly Ala Ser Val Val Ser Trp Ser Asp Val Ile
90              95              100

Val Ala Cys Ala Pro Trp Gln His Trp Asn Val Leu Glu Lys Thr
105             110             115
```

```
Glu  Glu  Ala  Glu  Lys  Thr  Pro  Val  Gly  Ser  Cys  Phe  Leu  Ala  Gln
120                 125                      130

Pro  Glu  Ser  Gly  Arg  Arg  Ala  Glu  Tyr  Ser  Pro  Cys  Arg  Gly  Asn
135                 140                      145

Thr  Leu  Ser  Arg  Ile  Tyr  Val  Glu  Asn  Asp  Phe  Ser  Trp  Asp  Lys
150                 155                      160

Arg  Tyr  Cys  Glu  Ala  Gly  Phe  Ser  Ser  Val  Thr  Gln  Ala  Gly
165                 170                      175

Glu  Leu  Val  Leu  Gly  Ala  Pro  Gly  Gly  Tyr  Tyr  Phe  Leu  Gly  Leu
180                 185                      190

Leu  Ala  Gln  Ala  Pro  Val  Ala  Asp  Ile  Phe  Ser  Ser  Tyr  Arg  Pro
195                 200                      205

Gly  Ile  Leu  Leu  Trp  His  Val  Ser  Ser  Gln  Ser  Leu  Ser  Phe  Asp
210                 215                      220

Ser  Ser  Asn  Pro  Glu  Tyr  Phe  Asp  Gly  Tyr  Trp  Gly  Tyr  Ser  Val
225                 230                      235

Ala  Val  Gly  Glu  Phe  Asp  Gly  Asp  Leu  Asn  Thr  Thr  Glu  Tyr  Val
240                 245                      250

Val  Gly  Ala  Pro  Thr  Trp  Ser  Trp  Thr  Leu  Gly  Ala  Val  Glu  Ile
255                 260                      265

Leu  Asp  Ser  Tyr  Tyr  Gln  Arg  Leu  His  Arg  Leu  Arg  Ala  Glu  Gln
270                 275                      280

Met  Ala  Ser  Tyr  Phe  Gly  His  Ser  Val  Ala  Val  Thr  Asp  Val  Asn
285                 290                      295

Gly  Asp  Gly  Arg  His  Asp  Leu  Leu  Val  Gly  Ala  Pro  Leu  Tyr  Met
300                 305                      310

Glu  Ser  Arg  Ala  Asp  Arg  Lys  Leu  Ala  Glu  Val  Gly  Arg  Val  Tyr
315                 320                      325

Leu  Phe  Leu  Gln  Pro  Arg  Gly  Pro  His  Ala  Leu  Gly  Ala  Pro  Ser
330                 335                      340

Leu  Leu  Leu  Thr  Gly  Thr  Gln  Leu  Tyr  Gly  Arg  Phe  Gly  Ser  Ala
345                 350                      355

Ile  Ala  Pro  Leu  Gly  Asp  Leu  Asp  Arg  Asp  Gly  Tyr  Asn  Asp  Ile
360                 365                      370

Ala  Val  Ala  Ala  Pro  Tyr  Gly  Gly  Pro  Ser  Gly  Arg  Gly  Gln  Val
375                 380                      385

Leu  Val  Phe  Leu  Gly  Gln  Ser  Glu  Gly  Leu  Arg  Ser  Arg  Pro  Ser
390                 395                      400

Gln  Val  Leu  Asp  Ser  Pro  Phe  Pro  Thr  Gly  Ser  Ala  Phe  Gly  Phe
405                 410                      415

Ser  Leu  Arg  Gly  Ala  Val  Asp  Ile  Asp  Asp  Asn  Gly  Tyr  Pro  Asp
420                 425                      430

Leu  Ile  Val  Gly  Ala  Tyr  Gly  Ala  Asn  Gln  Val  Ala  Val  Tyr  Arg
435                 440                      445

Ala  Gln  Pro  Val  Val  Lys  Ala  Ser  Val  Gln  Leu  Leu  Val  Gln  Asp
450                 455                      460

Ser  Leu  Asn  Pro  Ala  Val  Lys  Ser  Cys  Val  Leu  Pro  Gln  Thr  Lys
465                 470                      475

Thr  Pro  Val  Ser  Cys  Phe  Asn  Ile  Gln  Met  Cys  Val  Gly  Ala  Thr
480                 485                      490

Gly  His  Asn  Ile  Pro  Gln  Lys  Leu  Ser  Leu  Asn  Ala  Glu  Leu  Gln
495                 500                      505

Leu  Asp  Arg  Gln  Lys  Pro  Arg  Gln  Gly  Arg  Arg  Val  Leu  Leu  Leu
510                 515                      520
```

```
Gly  Ser  Gln  Gln  Ala  Gly  Thr  Thr  Leu  Asn  Leu  Asp  Leu  Gly  Gly
525                      530                      535

Lys  His  Ser  Pro  Ile  Cys  His  Thr  Thr  Met  Ala  Phe  Leu  Arg  Asp
540                      545                      550

Glu  Ala  Asp  Phe  Arg  Asp  Lys  Leu  Ser  Pro  Ile  Val  Leu  Ser  Leu
555                      560                      565

Asn  Val  Ser  Leu  Pro  Pro  Thr  Glu  Ala  Gly  Met  Ala  Pro  Ala  Val
570                      575                      580

Val  Leu  His  Gly  Asp  Thr  His  Val  Gln  Glu  Gln  Thr  Arg  Ile  Val
585                      590                      595

Leu  Asp  Cys  Gly  Glu  Asp  Val  Cys  Val  Pro  Gln  Leu  Gln  Leu
600                      605                      610

Thr  Ala  Ser  Val  Thr  Gly  Ser  Pro  Leu  Leu  Val  Gly  Ala  Asp  Asn
615                      620                      625

Val  Leu  Glu  Leu  Gln  Met  Asp  Ala  Ala  Asn  Glu  Gly  Glu  Gly  Ala
630                      635                      640

Tyr  Glu  Ala  Glu  Leu  Ala  Val  His  Leu  Pro  Gln  Gly  Ala  His  Tyr
645                      650                      655

Met  Arg  Ala  Leu  Ser  Asn  Val  Glu  Gly  Phe  Glu  Arg  Leu  Ile  Cys
660                      665                      670

Asn  Gln  Lys  Lys  Glu  Asn  Glu  Thr  Arg  Val  Val  Leu  Cys  Glu  Leu
675                      680                      685

Gly  Asn  Pro  Met  Lys  Lys  Asn  Ala  Gln  Ile  Gly  Ile  Ala  Met  Leu
690                      695                      700

Val  Ser  Val  Gly  Asn  Leu  Glu  Glu  Ala  Gly  Glu  Ser  Val  Ser  Phe
705                      710                      715

Gln  Leu  Gln  Ile  Arg  Ser  Lys  Asn  Ser  Gln  Asn  Pro  Asn  Ser  Lys
720                      725                      730

Ile  Val  Leu  Leu  Asp  Val  Pro  Val  Arg  Ala  Glu  Ala  Gln  Val  Glu
735                      740                      745

Leu  Arg  Gly  Asn  Ser  Phe  Pro  Ala  Ser  Leu  Val  Val  Ala  Ala  Glu
750                      755                      760

Glu  Gly  Glu  Arg  Glu  Gln  Asn  Ser  Leu  Asp  Ser  Trp  Gly  Pro  Lys
765                      770                      775

Val  Glu  His  Thr  Tyr  Glu  Leu  His  Asn  Asn  Gly  Pro  Gly  Thr  Val
780                      785                      790

Asn  Gly  Leu  His  Leu  Ser  Ile  His  Leu  Pro  Gly  Gln  Ser  Gln  Pro
795                      800                      805

Ser  Asp  Leu  Leu  Tyr  Ile  Leu  Asp  Ile  Gln  Pro  Gln  Gly  Gly  Leu
810                      815                      820

Gln  Cys  Phe  Pro  Gln  Pro  Pro  Val  Asn  Pro  Leu  Lys  Val  Asp  Trp
825                      830                      835

Gly  Leu  Pro  Ile  Pro  Ser  Pro  Ser  Pro  Ile  His  Pro  Ala  His  His
840                      845                      850

Lys  Arg  Asp  Arg  Arg  Gln  Ile  Phe  Leu  Pro  Glu  Pro  Glu  Gln  Pro
855                      860                      865

Ser  Arg  Leu  Gln  Asp  Pro  Val  Leu  Val  Ser  Cys  Asp  Ser  Ala  Pro
870                      875                      880

Cys  Thr  Val  Val  Gln  Cys  Asp  Leu  Gln  Glu  Met  Ala  Arg  Gly  Gln
885                      890                      895

Arg  Ala  Met  Val  Thr  Val  Leu  Ala  Phe  Leu  Trp  Leu  Pro  Ser  Leu
900                      905                      910

Tyr  Gln  Arg  Pro  Leu  Asp  Gln  Phe  Val  Leu  Gln  Ser  His  Ala  Trp
```

```
                    915                         920                          925
Phe  Asn  Val  Ser  Ser  Leu  Pro  Tyr  Ala  Val  Pro  Pro  Leu  Ser  Leu
930                      935                         940

Pro  Arg  Gly  Glu  Ala  Gln  Val  Trp  Thr  Gln  Leu  Leu  Arg  Ala  Leu
945                      950                         955

Glu  Glu  Arg
960       962
```

( 2 ) INFORMATION FOR SEQ ID NO:3:

( i ) SEQUENCE CHARACTERISTICS:
        ( A ) LENGTH: 2183 base pairs
        ( B ) TYPE: Nucleic Acid
        ( C ) STRANDEDNESS: Double
        ( D ) TOPOLOGY: Linear ( x i ) SEQUENCE DESCRIPTION: SEQ ID NO:3:

```
TCTAGAGCCG CC   ATG  AGA  GCA  CGT  CCT  CGA  CCA  CGT  CCT   39
                Met  Arg  Ala  Arg  Pro  Arg  Pro  Arg  Pro
                -26  -25                 -20

CTC  TGG  GCG  ACT  GTG  CTG  GCA  CTG  GGA  GCA  CTG  GCT  GGT   78
Leu  Trp  Ala  Thr  Val  Leu  Ala  Leu  Gly  Ala  Leu  Ala  Gly
          -15                 -10                             -5

GTT  GGA  GTA  GGA  GGG  CCC  AAC  ATC  TGT  ACC  ACG  CGA  GGT   117
Val  Gly  Val  Gly  Gly  Pro  Asn  Ile  Cys  Thr  Thr  Arg  Gly
                    1                   5

GTG  AGC  TCC  TGC  CAG  CAG  TGC  CTG  GCT  GTG  AGC  CCC  ATG   156
Val  Ser  Ser  Cys  Gln  Gln  Cys  Leu  Ala  Val  Ser  Pro  Met
10                       15                      20

TGT  GCC  TGG  TGC  TCT  GAT  GAG  GCC  CTG  CCT  CTG  GGC  TCA   195
Cys  Ala  Trp  Cys  Ser  Asp  Glu  Ala  Leu  Pro  Leu  Gly  Ser
          25                      30                           35

CCT  CGC  TGT  GAC  CTG  AAG  GAG  AAT  CTG  CTG  AAG  GAT  AAC   234
Pro  Arg  Cys  Asp  Leu  Lys  Glu  Asn  Leu  Leu  Lys  Asp  Asn
                    40                       45

TGT  GCC  CCA  GAA  TCC  ATC  GAG  TTC  CCA  GTG  AGT  GAG  GCC   273
Cys  Ala  Pro  Glu  Ser  Ile  Glu  Phe  Pro  Val  Ser  Glu  Ala
          50                      55                           60

CGA  GTA  CTA  GAG  GAC  AGG  CCC  CTC  AGC  GAC  AAG  GGC  TCT   312
Arg  Val  Leu  Glu  Asp  Arg  Pro  Leu  Ser  Asp  Lys  Gly  Ser
                    65                       70

GGA  GAC  AGC  TCC  CAG  GTC  ACT  CAA  GTC  AGT  CCC  CAG  AGG   351
Gly  Asp  Ser  Ser  Gln  Val  Thr  Gln  Val  Ser  Pro  Gln  Arg
75                       80                            85

ATT  GCA  CTC  CGG  CTC  CGG  CCA  GAT  GAT  TCG  AAG  AAT  TTC   390
Ile  Ala  Leu  Arg  Leu  Arg  Pro  Asp  Asp  Ser  Lys  Asn  Phe
          90                      95                          100

TCC  ATC  CAA  GTG  CGG  CAG  GTG  GAG  GAT  TAC  CCT  GTG  GAC   429
Ser  Ile  Gln  Val  Arg  Gln  Val  Glu  Asp  Tyr  Pro  Val  Asp
                    105                      110

ATC  TAC  TAC  TTG  ATG  GAC  CTG  TCT  TAC  TCC  ATG  AAG  GAT   468
Ile  Tyr  Tyr  Leu  Met  Asp  Leu  Ser  Tyr  Ser  Met  Lys  Asp
          115                      120                        125

GAT  CTG  TGG  AGC  ATC  CAG  AAC  CTG  GGT  ACC  AAG  CTG  GCC   507
Asp  Leu  Trp  Ser  Ile  Gln  Asn  Leu  Gly  Thr  Lys  Leu  Ala
               130                      135

ACC  CAG  ATG  CGA  AAG  CTC  ACC  AGT  AAC  CTG  CGG  ATT  GGC   546
Thr  Gln  Met  Arg  Lys  Leu  Thr  Ser  Asn  Leu  Arg  Ile  Gly
140                      145                           150

TTC  GGG  GCA  TTT  GTG  GAC  AAG  CCT  GTG  TCA  CCA  TAC  ATG   585
Phe  Gly  Ala  Phe  Val  Asp  Lys  Pro  Val  Ser  Pro  Tyr  Met
```

```
                          155                         160                              165
TAT  ATC  TCC  CCA  CCA  GAG  GCC  CTC  GAA  AAC  CCC  TGC  TAT   624
Tyr  Ile  Ser  Pro  Pro  Glu  Ala  Leu  Glu  Asn  Pro  Cys  Tyr
                    170                      175

GAT  ATG  AAG  ACC  ACC  TGC  TTG  CCC  ATG  TTT  GGC  TAC  AAA   663
Asp  Met  Lys  Thr  Thr  Cys  Leu  Pro  Met  Phe  Gly  Tyr  Lys
     180                           185                     190

CAC  GTG  CTG  ACG  CTA  ACT  GAC  CAG  GTG  ACC  CGC  TTC  AAT   702
His  Val  Leu  Thr  Leu  Thr  Asp  Gln  Val  Thr  Arg  Phe  Asn
               195                      200

GAG  GAA  GTG  AAG  AAG  CAG  AGT  GTG  TCA  CGG  AAC  CGA  GAT   741
Glu  Glu  Val  Lys  Lys  Gln  Ser  Val  Ser  Arg  Asn  Arg  Asp
205                      210                     215

GCC  CCA  GAG  GGT  GGC  TTT  GAT  GCC  ATC  ATG  CAG  GCT  ACA   780
Ala  Pro  Glu  Gly  Gly  Phe  Asp  Ala  Ile  Met  Gln  Ala  Thr
          220                      225                          230

GTC  TGT  GAT  GAA  AAG  ATT  GGC  TGG  AGG  AAT  GAT  GCA  TCC   819
Val  Cys  Asp  Glu  Lys  Ile  Gly  Trp  Arg  Asn  Asp  Ala  Ser
               235                      240

CAC  TTG  CTG  GTG  TTT  ACC  ACT  GAT  GCC  AAG  ACT  CAT  ATA   858
His  Leu  Leu  Val  Phe  Thr  Thr  Asp  Ala  Lys  Thr  His  Ile
245                      250                          255

GCA  TTG  GAC  GGA  AGG  CTG  GCA  GGC  ATT  GTC  CAG  CCT  AAT   897
Ala  Leu  Asp  Gly  Arg  Leu  Ala  Gly  Ile  Val  Gln  Pro  Asn
               260                      265

GAC  GGG  CAG  TGT  CAT  GTT  GGT  AGT  GAC  AAT  CAT  TAC  TCT   936
Asp  Gly  Gln  Cys  His  Val  Gly  Ser  Asp  Asn  His  Tyr  Ser
270                      275                     280

GCC  TCC  ACT  ACC  ATG  GAT  TAT  CCC  TCT  TTG  GGG  CTG  ATG   975
Ala  Ser  Thr  Thr  Met  Asp  Tyr  Pro  Ser  Leu  Gly  Leu  Met
          285                      290                          295

ACT  GAG  AAG  CTA  TCC  CAG  AAA  AAC  ATC  AAT  TTG  ATC  TTT  1014
Thr  Glu  Lys  Leu  Ser  Gln  Lys  Asn  Ile  Asn  Leu  Ile  Phe
               300                      305

GCA  GTG  ACT  GAA  AAT  GTA  GTC  AAT  CTC  TAT  CAG  AAC  TAT  1053
Ala  Val  Thr  Glu  Asn  Val  Val  Asn  Leu  Tyr  Gln  Asn  Tyr
     310                      315                     320

AGT  GAG  CTC  ATC  CCA  GGG  ACC  ACA  GTT  GGG  GTT  CTG  TCC  1092
Ser  Glu  Leu  Ile  Pro  Gly  Thr  Thr  Val  Gly  Val  Leu  Ser
               325                      330

ATG  GAT  TCC  AGC  AAT  GTC  CTC  CAG  CTC  ATT  GTT  GAT  GCT  1131
Met  Asp  Ser  Ser  Asn  Val  Leu  Gln  Leu  Ile  Val  Asp  Ala
335                      340                     345

TAT  GGG  AAA  ATC  CGT  TCT  AAA  GTA  GAG  CTG  GAA  GTG  CGT  1170
Tyr  Gly  Lys  Ile  Arg  Ser  Lys  Val  Glu  Leu  Glu  Val  Arg
          350                      355                          360

GAC  CTC  CCT  GAA  GAG  TTG  TCT  CTA  TCC  TTC  AAT  GCC  ACC  1209
Asp  Leu  Pro  Glu  Glu  Leu  Ser  Leu  Ser  Phe  Asn  Ala  Thr
               365                      370

TGC  CTC  AAC  AAT  GAG  GTC  ATC  CCT  GGC  CTC  AAG  TCT  TGT  1248
Cys  Leu  Asn  Asn  Glu  Val  Ile  Pro  Gly  Leu  Lys  Ser  Cys
375                      380                          385

ATG  GGA  CTC  AAG  ATT  GGA  GAC  ACG  GTG  AGC  TTC  AGC  ATT  1287
Met  Gly  Leu  Lys  Ile  Gly  Asp  Thr  Val  Ser  Phe  Ser  Ile
               390                      395

GAG  GCC  AAG  GTG  CGA  GGC  TGT  CCC  CAG  GAG  AAG  GAG  AAG  1326
Glu  Ala  Lys  Val  Arg  Gly  Cys  Pro  Gln  Glu  Lys  Glu  Lys
400                      405                     410

TCC  TTT  ACC  ATA  AAG  CCC  GTG  GGC  TTC  AAG  GAC  AGC  CTG  1365
Ser  Phe  Thr  Ile  Lys  Pro  Val  Gly  Phe  Lys  Asp  Ser  Leu
```

```
                              415                           420                                425
ATC GTC CAG GTC ACC TTT GAT TGT GAC TGT GCC TGC CAG                                                1404
Ile Val Gln Val Thr Phe Asp Cys Asp Cys Ala Cys Gln
                              430                                     435

GCC CAA GCT GAA CCT AAT AGC CAT CGC TGC AAC AAT GGC                                                1443
Ala Gln Ala Glu Pro Asn Ser His Arg Cys Asn Asn Gly
    440                                 445                                 450

AAT GGG ACC TTT GAG TGT GGG GTA TGC CGT TGT GGG CCT                                                1482
Asn Gly Thr Phe Glu Cys Gly Val Cys Arg Cys Gly Pro
                455                                 460

GGC TGG CTG GGA TCC CAG TGT GAG TGC TCA GAG GAG GAC                                                1521
Gly Trp Leu Gly Ser Gln Cys Glu Cys Ser Glu Glu Asp
465                             470                                 475

TAT CGC CCT TCC CAG CAG GAC GAG TGC AGC CCC CGA GAG                                                1560
Tyr Arg Pro Ser Gln Gln Asp Glu Cys Ser Pro Arg Glu
            480                                 485                             490

GGT CAG CCC GTC TGC AGC CAG CGG GGC GAG TGC CTC TGT                                                1599
Gly Gln Pro Val Cys Ser Gln Arg Gly Glu Cys Leu Cys
                    495                                 500

GGT CAA TGT GTC TGC CAC AGC AGT GAC TTT GGC AAG ATC                                                1638
Gly Gln Cys Val Cys His Ser Ser Asp Phe Gly Lys Ile
        505                                 510                             515

ACG GGC AAG TAC TGC GAG TGT GAC GAC TTC TCC TGT GTC                                                1677
Thr Gly Lys Tyr Cys Glu Cys Asp Asp Phe Ser Cys Val
                520                                 525

CGC TAC AAG GGG GAG ATG TGC TCA GGC CAT GGC CAG TGC                                                1716
Arg Tyr Lys Gly Glu Met Cys Ser Gly His Gly Gln Cys
530                                 535                             540

AGC TGT GGG GAC TGC CTG TGT GAC TCC GAC TGG ACC GGC                                                1755
Ser Cys Gly Asp Cys Leu Cys Asp Ser Asp Trp Thr Gly
            545                                 550                             555

TAC TAC TGC AAC TGT ACC ACG CGT ACT GAC ACC TGC ATG                                                1794
Tyr Tyr Cys Asn Cys Thr Thr Arg Thr Asp Thr Cys Met
                    560                                 565

TCC AGC AAT GGG CTG CTG TGC AGC GGC CGC GGC AAG TGT                                                1833
Ser Ser Asn Gly Leu Leu Cys Ser Gly Arg Gly Lys Cys
        570                                 575                             580

GAA TGT GGC AGC TGT GTC TGT ATC CAG CCG GGC TCC TAT                                                1872
Glu Cys Gly Ser Cys Val Cys Ile Gln Pro Gly Ser Tyr
                585                                 590

GGG GAC ACC TGT GAG AAG TGC CCC ACC TGC CCA GAT GCC                                                1911
Gly Asp Thr Cys Glu Lys Cys Pro Thr Cys Pro Asp Ala
595                                 600                             605

TGC ACC TTT AAG AAA GAA TGT GTG GAG TGT AAG AAG TTT                                                1950
Cys Thr Phe Lys Lys Glu Cys Val Glu Cys Lys Lys Phe
            610                                 615                             620

GAC CGG GAG CCC TAC ATG ACC GAA AAT ACC TGC AAC CGT                                                1989
Asp Arg Glu Pro Tyr Met Thr Glu Asn Thr Cys Asn Arg
                    625                                 630

TAC TGC CGT GAC GAG ATT GAG TCA GTG AAA GAG CTT AAG                                                2028
Tyr Cys Arg Asp Glu Ile Glu Ser Val Lys Glu Leu Lys
        635                                 640                             645

GAC ACT GGC AAG GAT GCA GTG AAT TGT ACC TAT AAG AAT                                                2067
Asp Thr Gly Lys Asp Ala Val Asn Cys Thr Tyr Lys Asn
                650                                 655

GAG GAT GAC TGT GTC GTC AGA TTC CAG TAC TAT GAA GAT                                                2106
Glu Asp Asp Cys Val Val Arg Phe Gln Tyr Tyr Glu Asp
660                                 665                             670

TCT AGT GGA AAG TCC ATC CTG TAT GTG GTA GAA GAG CCA                                                2145
Ser Ser Gly Lys Ser Ile Leu Tyr Val Val Glu Glu Pro
```

5,726,037

```
                   675                      680                        685
GAG  TGT  CCC  AAG  GGC  CCT  GAC  T GAT GAGATCTAAG  2180
Glu  Cys  Pro  Lys  Gly  Pro  Asp
                   690       692

CTT 2183
```

( 2 ) INFORMATION FOR SEQ ID NO:4:

( i ) SEQUENCE CHARACTERISTICS:
        ( A ) LENGTH: 718 amino acids
        ( B ) TYPE: Amino Acid
        ( D ) TOPOLOGY: Linear ( x i ) SEQUENCE DESCRIPTION: SEQ ID NO:4:

```
Met  Arg  Ala  Arg  Pro  Arg  Pro  Arg  Pro  Leu  Trp  Ala  Thr  Val  Leu
-26  -25                 -20                      -15

Ala  Leu  Gly  Ala  Leu  Ala  Gly  Val  Gly  Val  Gly  Pro  Asn  Ile
     -10                 -5                        1

Cys  Thr  Thr  Arg  Gly  Val  Ser  Ser  Cys  Gln  Gln  Cys  Leu  Ala  Val
 5                       10                      15

Ser  Pro  Met  Cys  Ala  Trp  Cys  Ser  Asp  Glu  Ala  Leu  Pro  Leu  Gly
 20                      25                      30

Ser  Pro  Arg  Cys  Asp  Leu  Lys  Glu  Asn  Leu  Leu  Lys  Asp  Asn  Cys
 35                      40                      45

Ala  Pro  Glu  Ser  Ile  Glu  Phe  Pro  Val  Ser  Glu  Ala  Arg  Val  Leu
 50                      55                      60

Glu  Asp  Arg  Pro  Leu  Ser  Asp  Lys  Gly  Ser  Gly  Asp  Ser  Ser  Gln
 65                      70                      75

Val  Thr  Gln  Val  Ser  Pro  Gln  Arg  Ile  Ala  Leu  Arg  Leu  Arg  Pro
 80                      85                      90

Asp  Asp  Ser  Lys  Asn  Phe  Ser  Ile  Gln  Val  Arg  Gln  Val  Glu  Asp
 95                     100                     105

Tyr  Pro  Val  Asp  Ile  Tyr  Tyr  Leu  Met  Asp  Leu  Ser  Tyr  Ser  Met
110                     115                     120

Lys  Asp  Asp  Leu  Trp  Ser  Ile  Gln  Asn  Leu  Gly  Thr  Lys  Leu  Ala
125                     130                     135

Thr  Gln  Met  Arg  Lys  Leu  Thr  Ser  Asn  Leu  Arg  Ile  Gly  Phe  Gly
140                     145                     150

Ala  Phe  Val  Asp  Lys  Pro  Val  Ser  Pro  Tyr  Met  Tyr  Ile  Ser  Pro
155                     160                     165

Pro  Glu  Ala  Leu  Glu  Asn  Pro  Cys  Tyr  Asp  Met  Lys  Thr  Thr  Cys
170                     175                     180

Leu  Pro  Met  Phe  Gly  Tyr  Lys  His  Val  Leu  Thr  Leu  Thr  Asp  Gln
185                     190                     195

Val  Thr  Arg  Phe  Asn  Glu  Glu  Val  Lys  Lys  Gln  Ser  Val  Ser  Arg
200                     205                     210

Asn  Arg  Asp  Ala  Pro  Glu  Gly  Gly  Phe  Asp  Ala  Ile  Met  Gln  Ala
215                     220                     225

Thr  Val  Cys  Asp  Glu  Lys  Ile  Gly  Trp  Arg  Asn  Asp  Ala  Ser  His
230                     235                     240

Leu  Leu  Val  Phe  Thr  Thr  Asp  Ala  Lys  Thr  His  Ile  Ala  Leu  Asp
245                     250                     255

Gly  Arg  Leu  Ala  Gly  Ile  Val  Gln  Pro  Asn  Asp  Gly  Gln  Cys  His
260                     265                     270

Val  Gly  Ser  Asp  Asn  His  Tyr  Ser  Ala  Ser  Thr  Thr  Met  Asp  Tyr
275                     280                     285
```

| | | | | | | | | | | | | |
|---|---|---|---|---|---|---|---|---|---|---|---|---|
| Pro 290 | Ser | Leu | Gly | Leu | Met 295 | Thr | Glu | Lys | Leu | Ser 300 | Gln | Lys | Asn | Ile |
| Asn 305 | Leu | Ile | Phe | Ala | Val 310 | Thr | Glu | Asn | Val | Val 315 | Asn | Leu | Tyr | Gln |
| Asn 320 | Tyr | Ser | Glu | Leu | Ile 325 | Pro | Gly | Thr | Thr | Val 330 | Gly | Val | Leu | Ser |
| Met 335 | Asp | Ser | Ser | Asn | Val 340 | Leu | Gln | Leu | Ile | Val 345 | Asp | Ala | Tyr | Gly |
| Lys 350 | Ile | Arg | Ser | Lys | Val 355 | Glu | Leu | Glu | Val | Arg 360 | Asp | Leu | Pro | Glu |
| Glu 365 | Leu | Ser | Leu | Ser | Phe 370 | Asn | Ala | Thr | Cys | Leu 375 | Asn | Asn | Glu | Val |
| Ile 380 | Pro | Gly | Leu | Lys | Ser 385 | Cys | Met | Gly | Leu | Lys 390 | Ile | Gly | Asp | Thr |
| Val 395 | Ser | Phe | Ser | Ile | Glu 400 | Ala | Lys | Val | Arg | Gly 405 | Cys | Pro | Gln | Glu |
| Lys 410 | Glu | Lys | Ser | Phe | Thr 415 | Ile | Lys | Pro | Val | Gly 420 | Phe | Lys | Asp | Ser |
| Leu 425 | Ile | Val | Gln | Val | Thr 430 | Phe | Asp | Cys | Asp | Cys 435 | Ala | Cys | Gln | Ala |
| Gln 440 | Ala | Glu | Pro | Asn | Ser 445 | His | Arg | Cys | Asn | Asn 450 | Gly | Asn | Gly | Thr |
| Phe 455 | Glu | Cys | Gly | Val | Cys 460 | Arg | Cys | Gly | Pro | Gly 465 | Trp | Leu | Gly | Ser |
| Gln 470 | Cys | Glu | Cys | Ser | Glu 475 | Glu | Asp | Tyr | Arg | Pro 480 | Ser | Gln | Gln | Asp |
| Glu 485 | Cys | Ser | Pro | Arg | Glu 490 | Gly | Gln | Pro | Val | Cys 495 | Ser | Gln | Arg | Gly |
| Glu 500 | Cys | Leu | Cys | Gly | Gln 505 | Cys | Val | Cys | His | Ser 510 | Ser | Asp | Phe | Gly |
| Lys 515 | Ile | Thr | Gly | Lys | Tyr 520 | Cys | Glu | Cys | Asp | Asp 525 | Phe | Ser | Cys | Val |
| Arg 530 | Tyr | Lys | Gly | Glu | Met 535 | Cys | Ser | Gly | His | Gly 540 | Gln | Cys | Ser | Cys |
| Gly 545 | Asp | Cys | Leu | Cys | Asp 550 | Ser | Asp | Trp | Thr | Gly 555 | Tyr | Tyr | Cys | Asn |
| Cys 560 | Thr | Thr | Arg | Thr | Asp 565 | Thr | Cys | Met | Ser | Ser 570 | Asn | Gly | Leu | Leu |
| Cys 575 | Ser | Gly | Arg | Gly | Lys 580 | Cys | Glu | Cys | Gly | Ser 585 | Cys | Val | Cys | Ile |
| Gln 590 | Pro | Gly | Ser | Tyr | Gly 595 | Asp | Thr | Cys | Glu | Lys 600 | Cys | Pro | Thr | Cys |
| Pro 605 | Asp | Ala | Cys | Thr | Phe 610 | Lys | Lys | Glu | Cys | Val 615 | Glu | Cys | Lys | Lys |
| Phe 620 | Asp | Arg | Glu | Pro | Tyr 625 | Met | Thr | Glu | Asn | Thr 630 | Cys | Asn | Arg | Tyr |
| Cys 635 | Arg | Asp | Glu | Ile | Glu 640 | Ser | Val | Lys | Glu | Leu 645 | Lys | Asp | Thr | Gly |
| Lys 650 | Asp | Ala | Val | Asn | Cys 655 | Thr | Tyr | Lys | Asn | Glu 660 | Asp | Asp | Cys | Val |
| Val 665 | Arg | Phe | Gln | Tyr | Tyr 670 | Glu | Asp | Ser | Ser | Gly 675 | Lys | Ser | Ile | Leu |
| Tyr | Val | Val | Glu | Glu | Pro | Glu | Cys | Pro | Lys | Gly | Pro | Asp | | |

(2) INFORMATION FOR SEQ ID NO:5:

(i) SEQUENCE CHARACTERISTICS:
        (A) LENGTH: 100 base pairs
        (B) TYPE: Nucleic Acid
        (C) STRANDEDNESS: Single
        (D) TOPOLOGY: Linear (xi) SEQUENCE DESCRIPTION: SEQ ID NO:5:

```
GAATTCTAGA GCCGCCATGA GAGCACGTCC TCGACCACGT CCTCTCTGGG   50
CGACTGTGCT GGCACTGGGA GCACTGGCTG GTGTTGGAGT AGGAGGGCCC  100
```

(2) INFORMATION FOR SEQ ID NO:6:

(i) SEQUENCE CHARACTERISTICS:
        (A) LENGTH: 104 base pairs
        (B) TYPE: Nucleic Acid
        (C) STRANDEDNESS: Single
        (D) TOPOLOGY: Linear (xi) SEQUENCE DESCRIPTION: SEQ ID NO:6:

```
CGCCGCGGGA GGCGGACGAG ATGCGAGCGC GGCCGCGGCC CCGGCCGCTC   50
TGGGCGACTG TGCTGGCGCT GGGGGCGCTG GCGGGCGTTG GCGTAGGAGG  100
GCCC  104
```

(2) INFORMATION FOR SEQ ID NO:7:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:7:

```
Leu Asn Leu Asp
 1           4
```

(2) INFORMATION FOR SEQ ID NO:8:

(i) SEQUENCE CHARACTERISTICS:
        (A) LENGTH: 39 base pairs
        (B) TYPE: Nucleic Acid
        (C) STRANDEDNESS: Double
        (D) TOPOLOGY: Linear (xi) SEQUENCE DESCRIPTION: SEQ ID NO:8:

```
CTGGCGGGCG TTGGCGTAGG AGGGCCCAAC ATCTGTACC   39
```

(2) INFORMATION FOR SEQ ID NO:9:

(i) SEQUENCE CHARACTERISTICS:
        (A) LENGTH: 98 base pairs
        (B) TYPE: Nucleic Acid
        (C) STRANDEDNESS: Single
        (D) TOPOLOGY: Linear (xi) SEQUENCE DESCRIPTION: SEQ ID NO:9:

```
AATTCTAGAG CCGCCATGAG AGCACGTCCT CGACCACGTC CTCTCTGGGC  50
GACTGTGCTG GCACTGGGAG CACTGGCTGG TGTTGGAGTA GGAGGCC     98
```

(2) INFORMATION FOR SEQ ID NO:10:

(i) SEQUENCE CHARACTERISTICS:
        (A) LENGTH: 90 base pairs (B) TYPE: Nucleic Acid
(C) STRANDEDNESS: Single
(D) TOPOLOGY: Linear (xi) SEQUENCE DESCRIPTION: SEQ ID NO:10:

CTCCTACTCC AACACCAGCC AGTGCTCCCA GTGCCAGCAC AGTCGCCCAG 50

AGAGGACGTG GTCGAGGACG TGCTCTCATG GCGGCTCTAG 90

(2) INFORMATION FOR SEQ ID NO:11:

(i) SEQUENCE CHARACTERISTICS:
(A) LENGTH: 9 amino acids
(B) TYPE: Amino Acid
(D) TOPOLOGY: Linear (xi) SEQUENCE DESCRIPTION: SEQ ID NO:11:

Leu Arg Ala Leu Glu Glu Arg Ala Ile
956             960             964

(2) INFORMATION FOR SEQ ID NO:12:

(i) SEQUENCE CHARACTERISTICS:
(A) LENGTH: 27 base pairs
(B) TYPE: Nucleic Acid
(C) STRANDEDNESS: Double
(D) TOPOLOGY: Linear (xi) SEQUENCE DESCRIPTION: SEQ ID NO:12:

CTCCGGGCCT TGGAGGAGAG GGCCATT 27

(2) INFORMATION FOR SEQ ID NO:13:

(i) SEQUENCE CHARACTERISTICS:
(A) LENGTH: 20 base pairs
(B) TYPE: Nucleic Acid
(C) STRANDEDNESS: Single
(D) TOPOLOGY: Linear (xi) SEQUENCE DESCRIPTION: SEQ ID NO:13:

CTTGGAGGAG AGGTGATGAA 20

(2) INFORMATION FOR SEQ ID NO:14:

(i) SEQUENCE CHARACTERISTICS:
(A) LENGTH: 20 base pairs
(B) TYPE: Nucleic Acid
(C) STRANDEDNESS: Single
(D) TOPOLOGY: Linear (xi) SEQUENCE DESCRIPTION: SEQ ID NO:14:

AGCTTTCATC ACCTCTCCTC 20

(2) INFORMATION FOR SEQ ID NO:15:

(i) SEQUENCE CHARACTERISTICS:
(A) LENGTH: 8 amino acids
(B) TYPE: Amino Acid
(D) TOPOLOGY: Linear (xi) SEQUENCE DESCRIPTION: SEQ ID NO:15:

Pro Lys Gly Pro Asp Ile Leu Leu
688     690             695

(2) INFORMATION FOR SEQ ID NO:16:

(i) SEQUENCE CHARACTERISTICS:
(A) LENGTH: 24 base pairs ( B ) TYPE: Nucleic Acid
        ( C ) STRANDEDNESS: Double
        ( D ) TOPOLOGY: Linear ( x i ) SEQUENCE DESCRIPTION: SEQ ID NO:16:

CCCAAGGGCC CTGACATCCT GGTG  24

( 2 ) INFORMATION FOR SEQ ID NO:17:

( i ) SEQUENCE CHARACTERISTICS:
        ( A ) LENGTH: 17 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:17:

CTGACTGATG AGATCTA  17

( 2 ) INFORMATION FOR SEQ ID NO:18:

( i ) SEQUENCE CHARACTERISTICS:
        ( A ) LENGTH: 25 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:18:

AGCTTAGATC TCATCAGTCA GGGCC  25